US012716062B2

(12) United States Patent
Goldberg et al.

(10) Patent No.: US 12,716,062 B2
(45) Date of Patent: Aug. 25, 2026

(54) METHODS AND SYSTEMS FOR ISOLATING AND IDENTIFYING NUCLEIC ACID FROM A PLURALITY OF MICROORGANISMS AND VIRUSES

(71) Applicant: WISCONSIN ALUMNI RESEARCH FOUNDATION, Madison, WI (US)

(72) Inventors: Tony Goldberg, Madison, WI (US); Samuel D. Sibley, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 938 days.

(21) Appl. No.: 17/516,596

(22) Filed: Nov. 1, 2021

(65) Prior Publication Data

US 2022/0251537 A1 Aug. 11, 2022

Related U.S. Application Data

(63) Continuation of application No. 15/694,249, filed on Sep. 1, 2017, now Pat. No. 11,162,090.

(60) Provisional application No. 62/382,657, filed on Sep. 1, 2016, provisional application No. 62/382,755, filed on Sep. 1, 2016.

(51) Int. Cl.

| | |
|---|---|
| ***C12N 15/10*** | (2006.01) |
| ***C12Q 1/6806*** | (2018.01) |
| ***C12Q 1/6853*** | (2018.01) |
| ***C12Q 1/686*** | (2018.01) |
| ***C12Q 1/6869*** | (2018.01) |
| ***C12Q 1/6888*** | (2018.01) |
| ***G16B 30/00*** | (2019.01) |
| ***G16B 50/00*** | (2019.01) |
| ***G16B 50/10*** | (2019.01) |
| ***G16B 50/30*** | (2019.01) |

(52) U.S. Cl.
CPC ....... *C12N 15/1003* (2013.01); *C12Q 1/6806* (2013.01); *C12Q 1/6853* (2013.01); *C12Q 1/686* (2013.01); *C12Q 1/6869* (2013.01); *G16B 30/00* (2019.02); *G16B 50/00* (2019.02); *G16B 50/10* (2019.02); *G16B 50/30* (2019.02); *C12Q 1/6888* (2013.01)

(58) Field of Classification Search
CPC ......................... C12N 15/1003; C12Q 1/6806; C12Q 1/6853; C12Q 1/686; C12Q 1/6869; C12Q 1/6888
See application file for complete search history.

(56) References Cited

PUBLICATIONS

Cipriano R (2011) Far from superficial: microbial diversity associated with the dermal mucus of fish. In: Cipriano, R, Schelkunov, I (eds.) Health and Diseases of Aquatic Organisms: Bilateral Perspectives. MSU Press, East Lansing, MI, pp. 156-167 (Year: 2011).*
Du et al. (Aquaculture, 2007, 262:532-534) (Year: 2007).*

(Continued)

*Primary Examiner* — Jeremy C Flinders
(74) *Attorney, Agent, or Firm* — McDonnell Boehnen Hulbert & Berghoff LLP

(57) ABSTRACT

Metagenomic data are increasingly useful for detecting microbes, such as viruses and other microorganisms in a wide range of sample types. Methods and systems for isolating, detecting, and characterizing microbes in biological samples using metagenomic data are provided. Also disclosed are methods for identifying microbes in nucleic acid libraries.

21 Claims, 11 Drawing Sheets

(56) References Cited

PUBLICATIONS

Iscotables (Year: 2015).*

Adhikari, B. N., A. C. Paskey, K. G. Frey, A. J. Bennett, K. A. Long, J. H. Kuhn, T. Hamilton, L. Glang, R. Z. Cer, T. L. Goldberg and K. A. Bishop-Lilly (2024). Virome profiling of fig wasps (*Ceratosolen* spp.) reveals virus diversity spanning four realms. Virology 591: 109992.

Campbell, L. J., N. A. Castillo, C. D. Dunn, A. Perez, J. J. Schmitter-Soto, S. C. Mejri, R. E. Boucek, R. S. Corujo, A. J. Adams, J. S. Rehage and T. L. Goldberg (2023). Viruses of Atlantic Bonefish (*Albula vulpes*) in Florida and the Caribbean show geographic patterns consistent with population declines. Environ Biol Fishes 106: 303-317.

Ford, C. E., C. D. Dunn, E. M. Leis, W. A. Thiel and T. L. Goldberg (2024). Five species of wild freshwater sport fish in Wisconsin, USA, reveal highly diverse viromes. Pathogens 13(2): 150.

Goldberg, T. L., A. J. Bennett, R. Kityo, J. H. Kuhn and C. A. Chapman (2017). Kanyawara virus: a novel Rhabdovirus infecting newly discovered nycteribiid bat flies infesting previously unknown pteropodid bats in Uganda. Sci Rep 7(1): 5287.

Goldberg, T. L., A. U. Perez and L. J. Campbell (2024). Isopods infesting Atlantic bonefish (*Albula vulpes*) host novel viruses, including reoviruses related to global pathogens, and opportunistically feed on humans. Parasitology: 1-39.

Goldberg, T. L., S. D. Sibley, M. E. Pinkerton, C. D. Dunn, L. J. Long, L. C. White and S. D. Strom (2019). Multidecade mortality and a homolog of hepatitis C virus in bald eagles (*Haliaeetus leucocephalus*), the national bird of the USA. Sci Rep 9: 14953.

Goldberg, T. L., V. L. Clyde, A. Gendron-Fitzpatrick, S. D. Sibley and R. Wallace (2018). Severe neurologic disease and chick mortality in crested screamers (*Chauna torquata*) infected with a novel Gyrovirus. Virology 520: 111-115.

Kamani, J., J. Gonzalez-Miguel, E. G. Msheliza and T. L. Goldberg (2022). Straw-colored fruit bats (Eidolon helvum) and their bat flies (*Cyclopodia greefi*) in Nigeria host viruses with multifarious modes of transmission. Vector Borne Zoonotic Dis 22(11): 545-552.

Lawrence, J. E. & G. F. Steward (2010). Purification of viruses by centrifugation. Manual of Aquatic Viral Ecology 17: 166-181.

Leis, E., R. Katona, S. Dziki, R. McCann, I. Standish, E. Opgenorth, A. Dikkeboom, A. Lim, C. E. Ford and T. L. Goldberg (2024). Novel Aquareovirus isolated from channel catfish (*Ictalurus punctatus*) used in mussel restoration efforts in Wisconsin. J Fish Dis: e13938.

Ramírez-Martinez, M. M., A. J. Bennett, C. D. Dunn, T. M. Yuill and T. L. Goldberg (2021). Bat flies of the family Streblidae (Diptera: Hippoboscoidea) host relatives of medically and agriculturally important "bat-associated" viruses. Viruses 13(5): 860.

Richard, J. C., E. Blevins, C. D. Dunn, E. M. Leis and T. L. Goldberg (2023). Viruses of freshwater mussels during mass mortality events in Oregon and Washington, USA. Viruses 15(8): 1719.

Richard, J. C., E. Leis, C. D. Dunn, R. Agbalog, D. Waller, S. Knowles, J. Putnam and T. L. Goldberg (2020). Mass mortality in freshwater mussels (*Actinonaias pectorosa*) in the Clinch River, USA, linked to a novel densovirus. Sci Rep 10(1): 14498.

Richard, J. C., E. M. Leis, C. D. Dunn, C. Harris, R. E. Agbalog, L. J. Campbell, S. Knowles, D. L. Waller, J. G. Putnam and T. L. Goldberg (2022). Freshwater mussels show elevated viral richness and intensity during a mortality event. Viruses 14(12): 2603.

Richard, J. C., T. W. Lane, R. E. Agbalog, S. L. Colletti, T. C. Leach, C. D. Dunn, N. Bollig, A. R. Plate, J. T. Munoz, E. M. Leis, S. Knowles, I. F. Standish, D. L. Waller and T. L. Goldberg (2024). Freshwater mussel viromes increase rapidly in diversity and abundance when hosts are released from captivity into the wild. Animals 14(17): 2531.

Sibley, S. D., M. A. Finley, B. B. Baker, C. Puzach, A. G. Armien, D. Giehtbrock and T. L. Goldberg (2016). Novel reovirus associated with epidemic mortality in wild largemouth bass (*Micropterus salmoides*). J Gen Virol 97(10): 2482-2487.

* cited by examiner

Results: 100x LOD

Virus

400

METHODS AND SYSTEMS FOR ISOLATING AND IDENTIFYING NUCLEIC ACID FROM A PLURALITY OF MICROORGANISMS AND VIRUSES

CROSS-REFERENCE TO RELATED APPLICATIONS

This patent application is a continuation application of U.S. patent application Ser. No. 15/694,249, filed Sep. 1, 2017, now U.S. Pat. No. 11,162,090 which claims the benefit of U.S. Provisional Patent Application Nos. 62/382,657 filed Sep. 1, 2016 and 62/382,755 filed Sep. 1, 2016, the disclosures of each of which are explicitly incorporated herein in their entirety by reference.

GOVERNMENT LICENSE RIGHTS

This invention was made with government support under AI098420 awarded by the National Institutes of Health. The government has certain rights in the invention.

BACKGROUND

Field of the Invention

The disclosure relates to laboratory and bioinformatics methods for isolating, detecting, and characterizing microbes in biological samples using metagenomic approaches.

Description of Related Art

Metagenomic data are increasingly useful for detecting microbes, such as viruses and other microorganisms, in clinical samples, contaminating microbes in industrial samples, and other microbes in various sample types. To date, however, most methods rely on PCR amplification of established microbial marker genes (e.g. bacterial 16S ribosomal RNA) for which large, curated databases have been established. Those methods are limited because amplifying the markers, and focusing only on established markers, potentially introduces quantitative or qualitative bias. As a result, the level of a microbial nucleic acid in a sample may be under- or over-estimated, or missed entirely. Thus, there is a need in the art for methods capable of detecting substantially all of the nucleic acids derived from a population of microbes. Furthermore, there is a need in the art for methods of preparing such nucleic acids in a manner that does not quantitatively or qualitatively bias the results.

Currently, however, no robust method exists for simultaneously isolating the nucleic acid of all viruses and microorganisms in a sample, while reducing or removing host materials, towards the goal of microbial identification inter alia via metagenomics. As a consequence, many microorganisms in a given sample are not detected, even by metagenomics, following conventional sample preparation methods. Therefore, there is a need to enrich biological samples for viruses and microorganisms prior to nucleic acid extraction. The need arises from the fact that microbial nucleic acid, including viral or other microorganism nucleic acid, in a sample is often orders of magnitude less concentrated than nucleic acid from the host or associated sources. Current methods yield insufficient viral or other microorganism nucleic acids (relative to other nucleic acids) for "unbiased" diagnostics, such as the metagenomics-based method described herein.

Moreover, it is generally believed that "ultracentrifugation" at speeds greater than 60,000×g is necessary to isolate certain viruses, necessitating costly equipment and rate-limiting preparation times. Thus, there is a need in the art for methods of isolating nucleic acids, such as nucleic acids from a virus or other microorganism, using less force produced at lower centrifugation speeds compatible with rapid and cost-effective clinical and analytical metagenomic analyses.

One of the further barriers to metagenomic analysis is efficiently processing and evaluating data for the presence of microbial sequences. At this time, genome sequencing is being used as a last resort for identifying microbes in samples, due to various complications and inefficiencies associated with current methods.

Accordingly, there is a need in the art for methods that differentially concentrate the nucleic acid of substantially all microbes, such as viruses and other microorganisms, present in a sample. Furthermore, there is a need in the art for methods of generating libraries of such nucleic acids to interrogate for the presence of microbes in a sample. Still further, there is a need in the art for methods of interrogating libraries of nucleic acids in order to identify microbes present therein.

SUMMARY OF THE INVENTION

The disclosure provides laboratory and bioinformatics methods and systems for isolating, detecting, and characterizing microbes in biological samples. In some embodiments, the disclosure provides laboratory and bioinformatics methods and systems useful in metagenomic approaches. In some aspects, the disclosure provides diagnostic or therapeutic clinical modalities based on rapid and inexpensive metagenomics pathogen analysis. In certain embodiments, the methods of the disclosure have application in veterinary and human diagnostics, and the identification of contaminants for food safety, water safety, quality control purposes during industrial processes, or environmental analysis, for example, air, soil, and water analysis.

In another aspect, the disclosure provides methods for isolating, detecting, and characterizing viruses and other microbes in biological samples at centrifugation speeds within the limits of conventional laboratory equipment such as, inter alia, many bench-top centrifuges. Accordingly, certain embodiments of the disclosure provide methods that do not require ultracentrifugation for isolating, detecting, and characterizing viruses and other microorganisms in a sample, thus providing rapid and cost-effective methods compatible with clinical or industrial analytics, for example, using metagenomic methods.

In some embodiments, the disclosure provides methods for isolating nucleic acid from a plurality of viruses and other microorganisms, comprising obtaining a sample comprising biological materials, and subjecting the sample to a serial centrifugation procedure.

In certain embodiments, the serial centrifugation procedure according to the disclosure comprises (1) centrifuging the sample to a force from between about 8,000 to about 12,000×g, (2) isolating a first supernatant and a first pellet, (3) centrifuging said first supernatant to a force from between about 22,000 to about 35,000×g, and/or through a liquid centrifugation medium, and (4) isolating a second supernatant and a second pellet. In some embodiments, the first centrifugation is performed under conditions that subject the nucleic acid in the sample to a force of about 10,000×g, and the second centrifugation is performed under conditions that subject the nucleic acid in the sample to a force equal to or greater than 25,000×g in a density centrifugation medium.

In still further embodiments, the density centrifugation procedure of the disclosure comprises a centrifugation medium with a density of between 1.1 and 1.5 grams per cubic centimeter. In some embodiments, the density centrifugation medium is sucrose or OptiPrep™. In particular embodiments, the centrifugation medium of the disclosure comprises a 20% sucrose solution.

In additional embodiments, the disclosure provides methods for isolating nucleic acid from a plurality of viruses or other microorganisms, comprising obtaining a sample, and subjecting the sample to a serial centrifugation procedure. In certain embodiments, the sample is collected from a host organism. In particular embodiments, the host organism according to the disclosure is selected from a human or non-human mammal.

In yet other embodiments, the disclosure provides methods for isolating nucleic acid from a plurality of viruses or other microorganisms in blood, serum, tissue, plasma, saliva, fecal matter, soil, or water.

The present disclosure also provides methods for isolating nucleic acid from a plurality of viruses or other microorganisms, wherein the methods further comprise treating the pellets or supernatants following centrifugation with nucleases to remove unwanted nucleic acids. In certain embodiments, nuclease digestion comprises incubation with at least one of a DNA nuclease or a RNA nuclease.

In still other embodiments, the present disclosure provides methods for isolating mitochondrial nucleic acid from a plurality of eukaryotic microorganisms, comprising: (1) obtaining a sample from a host organism, (2) isolating nucleic acid from the sample, wherein isolating is performed to preferentially isolate circular nucleic acid species including mitochondrial DNA, (3) sequencing the isolated nucleic acids to generate a library of DNA sequences from the sample, (4) comparing the sequences present in the library to a database comprising mitochondrial genomes, or portion thereof, and thereby identifying microorganisms present in the sample. In certain embodiments, isolating circular mitochondrial nucleic acid from a host organism comprises centrifuging the sample to a force from between about 8,000 to around 12,000×g, isolating a supernatant and a pellet, and preferentially isolating the circular nucleic acids in the pellet or the supernatant. In some embodiments, preferentially isolating the circular nucleic acids comprises column chromatography or cesium chloride density gradient centrifugation.

Also provided are methods of purifying nucleic acid from a plurality of viruses or other microorganisms, wherein the nucleic acid is isolated or purified from any of the second supernatant, or the first or second pellet resulting from the serial centrifugation procedure. In embodiments, the isolated or purified nucleic acid from a plurality of microorganisms and viruses is DNA or RNA.

In another aspect, the methods of the disclosure include one or more DNA or RNA synthesis steps, and one or more sequencing steps, to generate a library of nucleic acids from a plurality of viruses or other microorganisms present in the sample. In certain embodiments, the method comprises (1) synthesizing a plurality of first DNA strands complementary to the nucleic acids present in a second supernatant, or a first or second pellet, generated according to the disclosure, (2) synthesizing a plurality of second DNA strands complementary to the first DNA strand, (3) purifying a plurality of double strand DNA molecules produced by the first and second strand synthesis steps, (4) fragmenting the DNA molecules, (5) adding 5' and 3' adapters or other modifications in preparation for DNA sequencing, and (6) sequencing the fragmented DNA molecules, wherein the fragmenting and sequencing steps generate a library of nucleic acid sequences from a plurality of viruses or other microorganisms present in the sample.

Furthermore, the methods and systems of the disclosure include one or more steps of comparing the plurality of DNA sequences comprising a library of nucleic acids present in the sample to a database of known sequences of microbes (e.g. viruses, bacteria, fungi, or eukaryotic parasites). In some embodiments, the library of nucleic acids is converted into amino acid sequences prior to the comparison step. Thus, the disclosure provides methods of translating nucleic acid sequences from raw sequencing reads and assembled continuous sequences (contigs) into amino acid sequences using 6-frame translation, and using such amino acid sequences to interrogate amino acid sequence databases containing amino acid sequences from a plurality of viruses or other microorganisms. The method further comprises detecting the presence of the viruses or other microorganisms in the biological sample when at least one amino acid sequence identified from the library is homologous or identical to an amino acid sequence found in the viral or other microorganism amino acid sequence database.

In other embodiments, the library of sequenced nucleic acids is searched for open reading frames, including paired-end reads that have been merged, and assembled nucleic acid contigs, and any open reading frames are translated into amino acid sequences in silico. Thus, amino acid sequences are provided to interrogate amino acid sequence databases containing amino acid sequences from a plurality of viruses or other microorganisms. These methods further comprise detecting the presence of a virus or other microorganism in a biological sample when at least one amino acid sequence identified from the library is found in the viral or microorganismal amino acid sequence database.

In some embodiments, the disclosure provides methods for preparing a library of nucleic acid from a plurality of viruses or other microorganisms, comprising: obtaining a biological sample from a host organism, subjecting the biological sample to a serial centrifugation procedure comprising: centrifuging the sample to a force from between about 8,000 and 12,000×g, isolating a first supernatant and a first pellet, centrifuging said first supernatant to a force from between about 18,000 and 30,000×g, and/or through a liquid centrifugation medium, isolating a second supernatant and a second pellet, removing residual host organism nucleic acid by exposing any of the second supernatant, or the first or second pellet, to nuclease digestion, and sequencing the DNA or RNA of the second supernatant, or the first or second pellet, to generate a library of nucleic acids from a plurality of microorganisms and viruses present in the sample.

In one aspect, methods are provided for analyzing the plurality of DNA sequences comprising a library of nucleic acids present in a sample of the disclosure. In certain embodiments, the method includes obtaining a biological sample from a host and obtaining nucleic acid sequence information from the biological sample. The method also includes determining a first portion of the nucleic acid sequence information that corresponds to a known host sequence. The method additionally includes translating a second portion of the nucleic acid sequence information into amino acid sequence information in at least one open reading frame. The method yet further includes determining a plurality of amino acid sequences based on the second portion of the nucleic acid sequence information. The method additionally includes curating a database comprising a plurality of entries, wherein each entry includes respective microbe amino acid sequences. Curating the database includes ignoring or removing at least a portion of the entries corresponding to redundant sequence information, wherein the redundant sequence information is similar to at least one other entry at a similarity level greater than a threshold similarity level. The method includes comparing at least a portion of the plurality of amino acid sequences to the amino acid sequences in the curated database. The method also includes determining, based on the comparison, with at least one corresponding confidence level that at least one microbe is present in the biological sample.

In another aspect, a system is provided. The system includes a user interface and a computing device with a memory and at least one processor. A database is stored in the memory and the database includes a plurality of entries. Each entry includes a respective microbe amino acid sequence. The at least one processor executes instructions stored in the memory so as to carry out operations. The operations include receiving nucleic acid sequence information and determining a first portion of the nucleic acid sequence information that corresponds to a known host sequence. The operations additionally include translating a second portion of the nucleic acid sequence information into amino acid sequence information in at least one open reading frame. The operations also include determining a plurality of amino acid sequences based on the second portion of the nucleic acid sequence information. The operations also include curating the database. Curating the database includes removing at least a portion of the entries corresponding to redundant sequence information, wherein the redundant sequence information is similar to at least one other entry at a similarity level greater than a threshold similarity level. The operations include comparing each protein sequence of the plurality of protein sequences to the curated database. The operations also include determining, based on the comparison, with at least one corresponding confidence level that at least one microbe is present in the biological sample. The operations yet further include displaying, via the user interface, the identity of the at least one microbe and the at least one corresponding confidence level.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description can be best understood when read in conjunction with the following drawings in which.

DETAILED DESCRIPTION

Figure 1:
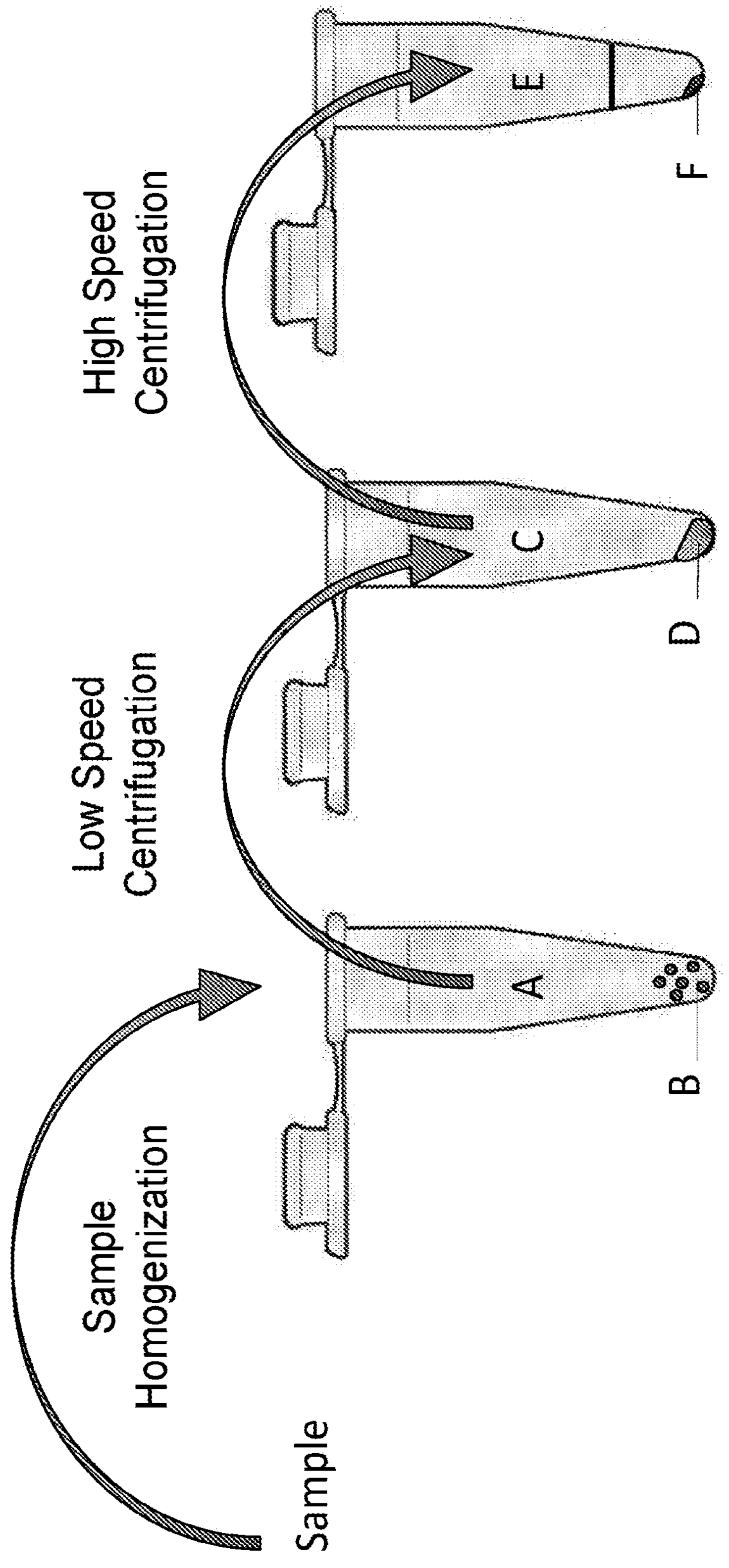
FIG. 1 shows an exemplary schematic of nucleic acid extraction for metagenomic pathogen detection. Sample is homogenized (label A), for example, by inert beads (label B), prior to a first centrifugation under conditions that subject the nucleic acid in the sample to a force of between about 8,000×g and 12,000×g. Label C indicates a first supernatant comprising clarified homogenate from low-speed centrifugation, comprising, inter alia, viruses, organelles, and free nucleic acid. Label D indicates a pellet resulting from a first centrifugation, comprising, inter alia, cellular and extracellular debris, bacteria, and parasites. Label E indicates a second supernatant after higher-speed centrifugation. The second supernatant comprises two fractions delineated by a dark grey line; a first fraction above the line consisting of, inter alia, cellular and extracellular debris, bacteria, and parasites and free nucleic acids, and a second fraction below the line consisting of a centrifugation density medium (e.g. sucrose, OptiPrep). The first fraction contains, e.g., free nucleic acids and proteins. The second fraction includes a pellet from the second (higher-speed) centrifugation (label F) comprising, inter alia, concentrated viruses.
Figure 2:
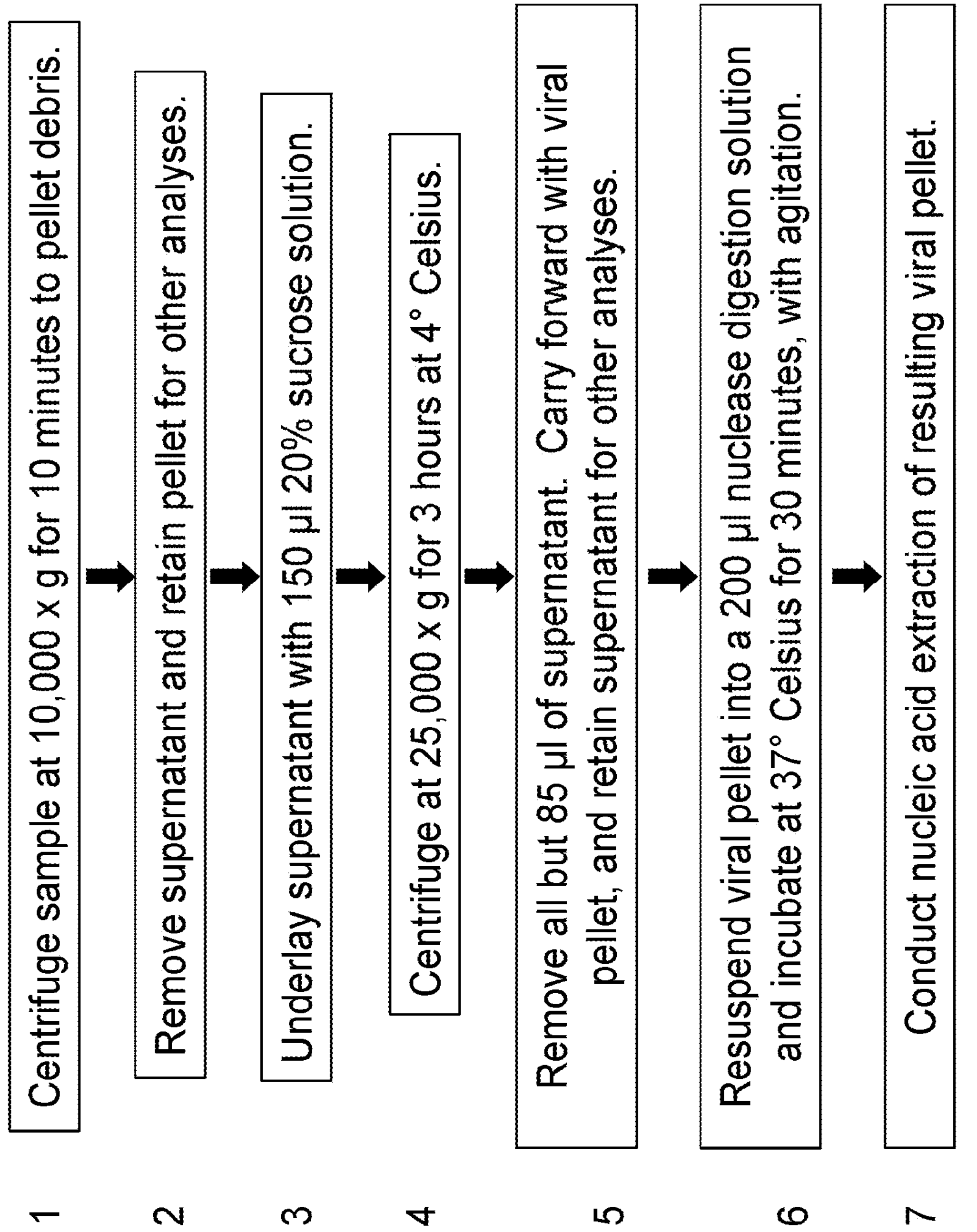
FIG. 2 shows a flow chart of sample preparation.

All publications, patents and patent applications cited herein are hereby expressly incorporated by reference for all purposes.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

Overview

The disclosure provides laboratory and bioinformatics methods and systems for isolating, detecting, and characterizing microbes, such as viruses and other microorganisms, in clinical samples, contaminating microbes in environmental or industrial samples, and other microbes in various sample types using metagenomic approaches. In some aspects, the disclosure provides diagnostic or therapeutic clinical modalities based on rapid and inexpensive metagenomics pathogen analysis. In other aspects, the disclosure provides means for epidemiological assessment of a population using rapid and inexpensive metagenomics pathogen analysis. In still further aspects, the disclosure provides means for assessing commercial populations of foodstuffs or livestock for the presence of infectious pathogens using rapid and inexpensive metagenomics pathogen analysis. In still further aspects, the disclosure provides means for assessing microbial contamination during industrial processes or during environmental assessment.

While the present disclosure describes embodiments for use ex vivo, one of skill in the art will also recognize that in vitro and in vivo applications are possible as well. Further, while embodiments disclosed herein make reference to use on or in conjunction with living animals, it is contemplated that the disclosed methods, systems, and devices can be used in any environment where obtaining rapid comparison results between sample amino acid sequences and reference amino acid sequences can be desirable. Specifically, embodiments described herein can provide information on dead animals (e.g., pathology) and/or industrial processes, such as food processing or other environments where rapid identification of microbial contaminants can be desirable.

Embodiments of the disclosure provide methods and reagents for the preparation of nucleic acids useful in metagenomic analysis. In some embodiments, the method comprises isolation of nucleic acids from viruses present in a sample. In other embodiments, the method comprises isolation of nucleic acids from bacterial species present in a sample. In still further embodiments, the method comprises isolation of nucleic acids from eukaryotic microorganisms and parasites present in a sample. Also provided are methods for isolating nucleic acids from all of viruses, eukaryotic parasites, and bacterial pathogens present in a sample.

In some embodiments, methods are provided for preparing libraries of nucleic acids derived from each of viruses, bacteria including pathogens, and eukaryotic microorganisms and parasites present in a sample. The libraries prepared according to methods of the embodiments are useful for performing metagenomics analyses to detect the presence or frequency of one or a plurality of microbes present in a sample.

Furthermore, methods and systems described herein can provide a metagenomic sequencing platform that is faster, less computationally intensive, and more sensitive than existing technology. Embodiments presented herein are also "unbiased," in the sense that, unlike existing technology, no prior information is needed about the microbes in a sample in order to apply the method.

Before describing the disclosed methods and compositions in detail, a number of terms will be defined. As used herein, the singular forms "a", "an", and "the" include plural referents unless the context clearly dictates otherwise. For example, reference to virus means one or more members of the same or a similar viral taxon (e.g. "influenza virus" referring to influenza types A, B, C, D, or other as-yet unidentified types).

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that are or are not utilized in a particular embodiment of this invention.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Techniques known to those skilled in the art are useful to practice methods disclosed herein. For example, the disclosure incorporates by reference all methods disclosed in Maniatis et al., in "Molecular Cloning—A Laboratory Manual (4$^{th}$ Ed)", Cold Spring Harbor Laboratory, (2012); Green, M. R. and Sambrook, P. M. (2014) *Molecular Cloning: A Laboratory Manual* (*Fourth Edition*), Cold Spring Harbor Laboratory Press, Cold Spring Harbor, NY; Burtis, C. A., Ashwood, E. R., and Bruns, D. E. (2013) *Tietz Textbook of Clinical Chemistry and Molecular Diagnostics, 5th Edition*. Saunders (Elsevier), St. Louis MO; Baxevanis, A. D. and Ouellette, B. F. F (editors) (2005) *Bioinformatics: A Practical Guide to the Analysis of Genes and Proteins,* 3*rd Edition*, Wiley, Hoboken, NJ, USA; de Bruijn, 2011. *Handbook of Molecular Microbial Ecology II: Metagenomics in Different Habitats*, Wiley-Blackwell, Hoboken, NJ; Knipe, D. M., and Howley, P. M (editors) (2014) *Fields Virology*, Lippincott Williams & Wilkins, Philadelphia, PA; Kwon, Y. M. and Ricke, S. C. (editors) (2011) *High-Throughput Next Generation Sequencing Methods and Applications*, Springer, New York, NY; Krawetz, Stephen A., Womble, David D. (Eds.) (2003) *Introduction to Bioinformatics: A Theoretical And Practical Approach*. Springer, New York; Streit, W, Daniel, R (editors) (2010) *Metagenomics Methods and Protocols*, Springer, New York, NY; World Organization for Animal Health (OIE) (2016) *Manual of Diagnostic Tests and Vaccines for Terrestrial Animals,* 8*th Edition*; Truant, A. L. (Ed.) (2016) *Manual of Commercial Methods in Clinical Microbiology International Edition,* 2*nd Edition*. Wiley-Blackwell.

As used herein, the term "microbe" comprises, for example, one or more bacteria, viruses and other microorganisms. As used herein, a microbe is any of a variety of different types, such as bacteria, fungi, viruses, mold, yeast, parasites, and others.

For example, the microbes of the disclosure can be one or more viruses, such as, without limitation: HIV, herpes simplex virus 1 (HSV 1), herpes simplex virus 2 (HSV 2), varicella zoster virus (herpes zoster), cytomegalovirus, Epstein Barr virus, papilloma virus, influenza virus, parainfluenza virus, adenovirus, West Nile virus, Zika virus, the agents of viral meningitis, arboviruses, arenaviruses, picornaviruses, coronaviruses, and syncytial viruses.

For example, the microbes of the disclosure can be one or more bacteria of a variety of different shapes, cell arrangements, and compositions. Most bacteria, for instance, have one of five basic cell shapes, i.e., (1) round or cocci, (2) rod or bacilli, (3) spiral or spirilli, (4) comma or vibrios, and (5) filaments. Likewise, examples of possible cell arrangements include diplococci (e.g., pair), streptococci (e.g., chain), and staphylococci (e.g., bunched). Diplococci, for example, are known to cause pneumonia. Streptococci are often associated with "strep throat." Staphylococci are familiar to many because of their role in "staph infections" and some types of food poisoning. Bacteria also vary somewhat in size, but generally average about 1/25,000 inch (about 1 micron) per bacteria.

In addition, the microbes of the disclosure comprise one or more types of fungi, such as molds and yeasts (e.g., *Candida albicans*). Zygomycota, for example, is a class of fungi that includes black bread mold and other molds that exhibit a symbiotic relationship with plants and animals. These molds are capable of fusing and forming tough "zygospores." Ascomycota is another class of fungi, which includes yeasts, powdery mildews, black and blue-green molds, and some species that cause diseases such as Dutch elm disease, apple scab, and ergot. Deuteromycota is another class of fungi that includes a miscellaneous collection of fungi that do not fit easily into the aforementioned classes or the Basidiomycota class (which includes most mushrooms, pore fungi, and puffball fungi). Deuteromycetes include the species that create cheese and penicillin, but also includes disease-causing members such as those that lead to athlete's foot and ringworm.

The microbes of the disclosure include, without limitation, *Plasmodium* parasites (e.g., *P. falciparum, P. vivax, P. malariae*, and *P. ovale*). The microbes of the disclosure also comprise, without limitation, protozoan parasites such as *Amoeba histolytica, Amoeba hartmanni, Amoeba coli, Amoeba nana, Giardia lamblia, Cryptosporidium* sp., *Blastocystis hominis, Chilomastix mesnili, Iodamoeba butschlii, Dientamoeba fragillis*, and non-protozoan parasites such as Platyhelminthes (flat worms): flukes (liver, intestines, lungs and blood) and tapeworms (intestines), Schistosomes, Nemathelminthes (round worms); Strongyloides, Trichuris, Trichinella, Pin worms, Ascaris, and hookworms.

Those skilled in the art will recognize additional microbes detectable by methods of the disclosure, though not specifically enumerated herein.

As used herein, the term "nucleic acid extraction" refers to the technique of processing a biological sample such that the nucleic acids contained within that sample are purified to the exclusion (or relative exclusion) of other components of the sample, such as proteins and carbohydrates. The goal of nucleic acid extraction is to obtain a substantially pure sample of nucleic acids (usually in an aqueous medium) that is suitable for analyses, such as genetic, genomic, or metagenomic DNA analysis or sequencing. Nucleic acid extraction is also sometimes referred to as nucleic acid "isolation."

As used herein, the terms "nucleic acid sequencing" or "DNA sequencing" refers to the process of determining the order of nucleotides (A, C, G, T/U, or alternative bases) along a strand of DNA or RNA. "Deep sequencing" or "next generation sequencing" or "massively parallel sequencing" and similar terms refer to a set of technologies used for sequencing many molecules of nucleic acid (millions or more) simultaneously, such that the resulting data are especially suitable for metagenomics. The term "shotgun sequencing" refers to a type of sequencing in which nucleic acids are fragmented prior to the sequencing reaction, sequences of a random subset of fragmented DNA molecules are generated, and the resulting sequences are assembled computationally.

As used herein, the terms "reads," or "sequencing reads," or the like, refer to individual DNA sequences inferred using nucleic acid sequencing technologies. These individual sequences represent the inferred nucleic acid sequence of an individual molecule in an original sample or its derivatives (e.g. copies of that molecule generated using any number of nucleic acid amplification methods). Reads are the "raw data" of nucleic acid sequencing technologies.

As used herein, the terms "library," "libraries," "nucleic acid library," "DNA library," or "RNA library" refer to collections of nucleic acid molecules that have been extracted from a sample and prepared for nucleic acid sequencing and metagenomics. Those terms also apply to the collections of sequences of the nucleic acids sequenced according to the present methods. Typically, the preparation of a library involves converting longer nucleic acids into shorter fragments (usually by physical or enzymatic means) and then attaching additional nucleic acids of known sequence to these molecules to make them suitable for sequencing on a "next generation" nucleic acid sequencing instrument. As used herein, the term "libraries" does not necessarily include in each instance preparing conventional collections of nucleic acid fragments in bacteriophage or plasmid vectors.

As used herein, "bioinformatics," refers to the application of computational tools to biological data in order to extract information. For example, comparing unknown nucleic acid sequences obtained using metagenomics to known nucleic acid sequences in a curated database requires computational methods involving thousands or millions of pairwise sequence comparisons. Computer programs designed to execute such methods would be classified as pertaining to "bioinformatics," and are designed to accomplish bioinformatics analyses.

As used herein, the term "metagenomics" refers to the study of nucleic acid from a population, such as bacteria, viruses or other microorganisms. Thus, metagenomics is used, for example, to infer certain properties of the constituent members of a population, such as their identities and/or relative or absolute frequencies. Metagenomics differs from traditional genetics and genomics in that it considers the plurality of organisms in a sample, rather than focusing on the genetic information from a single organism (genetics/genomics) or a set of related organisms (population genetics/population genomics). Technologically, metagenomics refers to the application of massively parallel (i.e. "deep") DNA sequencing technologies to targeted or random genomic regions in samples containing a diversity of organisms (usually, but not necessarily, microbes). Metagenomics is useful in fields including biochemistry, medicine, and ecology.

Sample Preparation

The methods of the disclosure are useful for determining the presence of microbes in biological samples derived from various materials. In some embodiments, a sample according to the disclosure is derived from biological material obtained from a subject. In some embodiments, the subject is a mammal. For example, in some embodiments a subject of the disclosure is a human or non-human mammal suffering from an unknown pathogenic condition, or a human or non-human mammal that died from such unknown pathogenic condition. In other embodiments, the sample of the disclosure is derived from materials potentially comprising pathogenic contaminants, such as, without limitation, a water sample, a soil sample, an air sample, a stool or fecal sample, or any sample where knowledge of the composition of potential microbes is useful. In still further embodiments, a sample of the disclosure is an industrial input, output, product or byproduct where knowledge of the composition of microbial contaminants is useful.

As used herein, a "sample" is comprised of material potentially containing microbes. In some embodiments, the material isolated from a living subject and includes, without limitation, blood, serum, tissue, plasma or blood cells. In some embodiments, the material is isolated from a dead organism, the environment, or an industrial or workplace setting and includes, without limitation, soil, air, water, swabs or other methods of collection of materials from surfaces, and any solid, liquid or gaseous input, output, product or byproduct of a production process. In some embodiments, the sample is frozen prior to nucleic acid isolation.

In some embodiments of the method, the nucleic acids of viruses, eukaryotic parasites, or bacterial pathogens are isolated from tissues homogenized prior to nucleic acid extraction. The tissue sample can be animal-, human-, or agricultural-originated tissue. Tissue homogenization is accomplished by methods known to the art. Conventional mechanical methods can be used to homogenize, or disrupt, tissues of the samples disclosed herein. These methods include: 1) using a motorized mechanical homogenizer that employs a component like a blender to generate shear force to physically break up solid tissues and release all intracellular components into the surrounding medium; 2) using a high-pressure homogenizer that employs impingement of high liquid shear force in orifice to disrupt the connections between cells in the tissue; 3) using a bead mill that breaks up connections between cells in a tissue by shear force generated due to grinding and collisions between beads; and 4) using a sonication device that employs ultrasonic waves to generate intense pressure waves with enough energy to break cell membranes.

In other embodiments, enzymatic methods are used to dissolve and/or dissociate tissues or cells prior to nucleic acid isolation. For example, the enzyme for tissue dissociation can be, without limitation, a protease, cellulase, lipase, or the like. Some proteases useful in the method are proteinase K, collagenase, trypsin, chymotripsin, elastase, papain, chymopapain, hyaluronidase, pronase, dispase, thermolysin, bromelain, cathespines, or pepsin, or a mixture thereof. In some embodiments, a mixture of enzymes, such as proteases, are used to homogenize tissues prior to nucleic acid isolation.

In some embodiments, eukaryotic or prokaryotic cells present in a sample are disrupted by lysis prior to nucleic acid isolation. For example, cell lysis according to the present disclosure is accomplished by mechanical, enzymatic, chemical, or other means, including the means used to homogenize tissues described supra.

In some embodiments, a sample of the disclosure is homogenized prior to isolating nucleic acids using a commercially available bead-based homogenizer. For example, a bench-top, bead-based homogenizer capable of rapid and efficient tissue homogenization and cell lysis is useful in methods of the disclosure. (See, e.g., BioSpec Products, MINI-BEAD BEATER; see also, Powerlyzer® 24 Bench Top Bead-Based Homogenizer, MoBio Laboratories, Inc.) In certain embodiments, hard beads are added to a sample of the disclosure prior to bead-based homogenization (e.g. MoBio, Inc. bead-beating tube, 2.0 mL, 2.38 mm metal beads, Cat. No. 13117-50). In particular embodiments, the beads of the disclosure can comprise metal, ceramic, garnet, glass, quartz, or other bead types known in the art, and suitable for the methods disclosed herein.

The samples of the present disclosure are prepared in suitable buffering solutions in order to preserve sample contents and protect them from degradation or alteration. For example, in some embodiments the samples are prepared in a Tris-NaCl-EDTA buffering system ("TNE buffer"; 50 mM Tris-HCl, 150 mM NaCl, 1 mM EDTA, pH 7.4). In other embodiments, samples of the present disclosure are prepared in Phosphate Buffered Saline, Hanks balanced salt solution, Eagle's minimum essential medium, or related media. In still further embodiments, samples of the present disclosure are prepared in buffers supplemented with enzyme inhibitors, such as protease or nuclease inhibitors, to prevent unwanted degradation of sample components, for example nuclease stabilizing solutions such as RNAlater™ (Ambion™, Cat. No. AM7020) (website) or DNA/RNA Shield™ (Zymo Research, Cat. No. R1100).

Serial Centrifugation

In certain embodiments, methods of the disclosure comprise a first centrifugation step wherein the sample of the disclosure is subjected to a centrifugal force and its components separated according to their sedimentation properties. The use of centrifuges has been summarized in the following books, the entire contents of which are incorporated by reference herein: *Centrifugal Separations in Biotechnology* by Wallace Woon-Fong Leung Academic Press; 1 edition (Aug. 30, 2007) (by reference and for industrial applications reviewed in *Perry's Chemical Engineers' Handbook* 8/*E Section* 18: *Liquid-Solid Operations and Equipment* McGraw-Hill Professional (Aug. 1, 2007); *Industrial Centrifugation Technology* by Wallace Woon-Fong Leung (Feb. 1, 1998); *Biological Centrifugation* (*The Basics*) by J. M. Graham (Oct. 15, 2001); *Refining iron-contaminated zinc by filtration and centrifugation* by John A. Ruppert (Jan. 1, 1967); *Processing by Centrifugation* by Liya L. Regel and William R. Wilcox (Sep. 1, 2001); *Centrifugation in Density Gradients* by C. A. Price (October 1982); *Decanter Centrifuge Handbook* by A. Records and K Sutherland (Mar. 16, 2001); *Bioseparations Science and Engineering* (*Topics in Chemical Engineering* (Oxford University Press) by Roger G. Harrison, Paul W. Todd, Scott R. Rudge, and Demetri Petrides (Oct. 31, 2002).

In particular embodiments, a sample of the disclosure is subjected to a means, such as a table top centrifuge, for separating an optionally homogenized sample based upon the physical properties of the species therein, thus yielding from the heterogeneous sample a sedimentation fraction comprising a first pellet, and a non-sedimentation fraction comprising a first supernatant. The force on the components subjected to centrifugation is described in reference to gravity and referred to as Relative Centrifugal Force (RCF). For example, an RCF of 500×g indicates that the centrifugal force applied is 500 times greater than Earth's gravitational force.

In certain embodiments, the first centrifugation step of the method subjects the sample to a force between about $5\times10^3\times g$ and about $15\times10^3\times g$. In other embodiments, the first centrifugation step of the method subjects the sample to a force between about $8\times10^3\times g$ and about $12\times10^3\times g$. In a particular embodiment, the first centrifugation step of the method subjects the sample to a force of $10\times10^3\times g$. In some embodiments, the first centrifugation step of the disclosure is conducted at 4° C.

In certain embodiments, the first centrifugation step subjects the sample to a specific RCF for about 1 to about 100 minutes, or alternately between about 5 to about 50 minutes, about 10 to about 30 minutes, or about 15 to about 25 minutes. In a particular embodiment, the first centrifugation step subjects the sample to a specific RCF for 10 minutes.

Usually the components in the sedimentation fraction will have similar sedimentation velocities. Thus, the first pellet comprises a population of, among other components, nucleic acids with similar sedimentation properties that are separated from the first non-sedimenting supernatant fraction. The first supernatant fraction, in turn, comprises a distinct, second population of nucleic acids with similar sedimentation properties. Each of the first pellet and first supernatant fractions are isolated from one another and used for subsequent steps of embodiments of the method.

In certain embodiments of the method, a first supernatant isolated from a first centrifugation step is subject to a second centrifugation step. In some embodiments, the first supernatant is further processed, e.g. enzymatically, immunologically, chemically, or otherwise, prior to the second centrifugation step. In other embodiments, the first supernatant is directly subjected to a second centrifugation step without additional processing. In some embodiments, the first supernatant is stored, e.g., frozen or lyophilized, prior to the second centrifugation step.

In particular embodiments, the second centrifugation step of the disclosure subjects the first supernatant to between about $18\times10^3\times g$ and about $30\times10^3\times g$. In other embodiments, the second centrifugation step of the disclosure subjects the first supernatant to between about $22\times10^3\times g$ and about $28\times10^3\times g$. In a particular embodiment, the second centrifugation step of the disclosure subjects the first supernatant to $25\times10^3\times g$. In embodiments, the second centrifugation step of the disclosure is conducted at 4° C.

In some embodiments, the second centrifugation step subjects the first supernatant to a specific RCF for about 50 to about 500 minutes, or alternately between about 75 to about 400 minutes, about 100 to about 350 minutes, or about 150 to about 200 minutes. In particular embodiments, the second centrifugation step subjects the first supernatant to a specific RCF for 180 minutes.

The second centrifugation step of methods of the disclosure optionally comprises a density centrifugation medium. In certain embodiments, materials such as sucrose, OptiPrep, or Ficoll, or salts such as NaCl, NaBr, or CsCl, are used for preparation of the density centrifugation medium. In some embodiments, the density medium comprises isopycnic (="same density") density gradient centrifugation. In isopycnic density gradient centrifugation, the density gradient column encompasses the whole range of densities of sample particles. Each particle will sediment only to the position in the gradient where the density in the gradient column equals its own density, and the particle will remain at this position in the density gradient.

In other embodiments, the density medium comprises a rate zonal density gradient medium. In rate zonal density gradient centrifugation, a sample solution containing particles to be fractionated is layered on top of a density gradient column. For example, a sucrose density gradient is prepared by pipetting layers of progressively lower concentrations of sucrose on top of higher concentrations into a centrifuge tube. Alternatively, density gradient columns are prepared using a syringe with a piece of tubing attached to the syringe needle (20-22 gauge). To prepare a 5-20% sucrose density gradient a given volume of 5% sucrose is placed in the tube, and then an equivalent volume of 10% sucrose is carefully injected the into the tube keeping the tip of the syringe tubing at the bottom of the centrifuge tube. The process is repeated with 15% of 20% sucrose. Ficoll and cesium chloride density gradients can be prepared in a similar manner. Density gradients thus prepared can either be used immediately as a step gradient or made into a linear gradient by allowing it to diffuse in a refrigerator overnight.

In certain embodiments, the density centrifugation medium of the disclosure comprises an isopycnic density between about 1.1 and about 2.0 grams per cubic centimeter. In some embodiments, the isopycnic density centrifugation medium of the disclosure comprises a density between about 1.3 and about 1.7 grams per cubic centimeter. In other embodiments, the isopycnic density centrifugation medium of the disclosure is about 1.5 grams per cubic centimeter. In still further embodiments, the centrifugation medium of the disclosure comprises a rate zonal, density gradient comprising a range of the above densities.

In particular embodiments, a density gradient according to the disclosure is an isopycnic density medium comprising 20% sucrose.

In methods of the disclosure comprising a second centrifugation using density centrifugation medium, some or all of the first supernatant is applied directly to the top of the centrifugation media in a tube. The tube is centrifuged according to the method disclosed above. In some embodiments, a second pellet is isolated by removing between about 90% and about 99% of the second supernatant fraction. Thus, embodiments of the disclosure provide a second pellet and a second supernatant containing subpopulations of nucleic acids with common sedimentation properties that were present in the optionally homogenized sample.

Nuclease Treatment

In some embodiments, the methods of the disclosure provide a nuclease treatment step, or a nuclease "digestion" step, wherein the sample, or fractions thereof, are exposed to a cleavage agent. The term "cleavage agent" as used herein refers to an agent, sometimes a chemical agent or an enzyme that can cleave a nucleic acid at one or more specific or non-specific sites. Specific cleavage agents often cleave specifically according to a particular nucleotide sequence at a particular site. In some cases, the nucleic acid is exposed to one or more cleavage agents prior to a centrifugation or amplification step. In some cases, the nucleic acid is exposed to one or more cleavage agents following a centrifugation or amplification step. In some cases, the nucleic acid is exposed to one or more cleavage agents both prior to and following one or more centrifugation or amplification step.

In certain embodiments, the nuclease treatment step is performed on a sample, or one or more of a sample, a first or second pellet, or a first or second supernatant. In this manner, unwanted nucleic acid contaminants are optionally removed, thus enriching for the microbially derived nucleic acids present in the sample, or fractions thereof. In some embodiments, the nuclease treatment step of the disclosure degrades non-encapsidated nucleic acid present in a sample, or fraction thereof, thereby degrading the contaminating nucleic acids (such as, for example, host nucleic acid) while leaving the encapsidated (for example, viral) nucleic acid intact.

In some embodiments, the nuclease treatment step of the method comprises treating the sample, or fraction thereof, with a cleavage agent comprising an enzyme having DNAse activity. In other embodiments, the nuclease treatment step of the method comprises treating the sample, or fraction thereof, with a cleavage agent comprising an enzyme having RNAse activity. In still other embodiments, the nuclease treatment step of the method comprises treating the sample, or fraction thereof, with cleavage agents comprising an enzyme mixture having both DNAse and RNAse activity.

Those skilled in the art will recognize suitable enzymes useful in a nuclease treatment step according to embodiments of the method. Examples of enzymatic cleavage agents include without limitation endonucleases (e.g., DNase (e.g., DNase I, II)); RNase (e.g., RNase E, F, H, P); CLEAVASE enzyme; TAQ DNA polymerase; *E. coli* DNA polymerase I and eukaryotic structure-specific endonucleases; murine FEN-1 endonucleases; restriction endonucleases (i.e. restriction enzymes) such as such as the Type I, Type II, Type IIS, Type IIG, Type III and Type IV enzymes; glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1, N6-etheno-adenine DNA glycosylase); exonucleases (e.g., exonuclease I, exonuclease II, exonuclease III, exonuclease IV, exonuclease V, exonuclease VI, exonuclease VII, exonuclease VIII); ribozymes, and DNAzymes.

In certain embodiments, the enzymatic cleavage agents of the disclosure comprise commercially available mixtures of DNAse, RNAse, or combinations thereof. For example, in some embodiments, a sample or fraction thereof, is exposed to RiboShredder™ RNase Blend (epicenter, Cat. No. RS12500). In other embodiments, a sample, or fraction thereof, is exposed to TURBO™ DNase (Ambion™, Cat. No. AM2238). In still further embodiments, a sample, or fraction thereof, is exposed to other commercially available DNAse and RNAse preparations, or combinations thereof.

In some embodiments, the method of the disclosure further comprises exposing a sample, or fraction thereof, to one or more agents capable of inactivating nuclease enzymes, such as a DNAse, RNAse, or combinations thereof, added to the sample. In some embodiments, the one or more agents capable of inactivating nuclease enzymes comprise commercially available DNA/RNA Shield™ (Zymo Research, Cat. No. R1100). Whereas standard nuclease inactivation is accomplished by heating or adding lysis buffer, nucleases retain residual activity even after these treatments. Accordingly, adding a volume of a DNA/RNA Shield reagent can inactivate nucleases immediately, providing more precise control of the reaction and increasing the sensitivity pathogen-derived nucleic acid isolation.

MitoBiome and Microbiome Analysis

In another aspect, the disclosure provides methods for isolating non-viral, microbial—including pathogen-derived—nucleic acid from a sample, or fraction thereof, comprising isolating circular, double stranded mitochondrial DNA (mtDNA) substantially free of genomic DNA (gDNA). For example, the methods of the disclosure comprise isolating intact, complete mitochondria for "MitoBiome" analysis, said method is capable of simultaneously identifying nucleic acid sequences from a plurality of eukaryotic organisms (e.g., mammals, parasites and fungi) present in a sample, based on comparison of those sequences to a database of mitochondrial sequences from known eukaryotic organisms. The methods of the disclosure further provide a library of nucleic acids comprising mitochondrial nucleic acids derived from a plurality of eukaryotic organisms (e.g., mammals, parasites and fungi) present in a sample.

In certain embodiments, the present disclosure provides "shotgun" sequencing of mitochondrial DNA that can be used to identify eukaryotic pathogens. Because mitochondrial DNA is circular (like a bacterial plasmid), there are well-developed chemistries for preferentially isolating mitochondrial DNA. For example, common "plasma prep" kits, which work on a wide diversity of principles, are useful in the methods of the disclosure. Other embodiments utilize alternative methods of preferentially isolating circular nucleic acid (such as mitochondrial DNA), such as cesium chloride density gradient centrifugation, alkaline lysis and ethanol precipitation, use of potassium xanthogenate-sodium dodecyl sulfate-phenol (XSP) buffer. Thus, embodiments of the disclosure isolate mitochondrial DNA using its unique biological properties, and then sequence the entire mitochondrial genome to identify the eukaryotic organisms in a sample.

Although there are known methods of using PCR on specific mitochondrial genes (e.g. cytochrome b) and sequencing the product to identify the organism, such "DNA barcoding" relies on PCR, which is inherently biased because it uses primers that anneal to specific, known DNA sequences to initiate polymerization. In contrast, methods of the present disclosure sequence mitochondrial DNA in an "unbiased" way, from starting material that is purposefully enriched for mitochondrial DNA.

In yet another aspect, the disclosure provides methods for isolating non-viral, pathogen-derived nucleic acid from a sample, or fraction thereof, comprising bacterial-derived nucleic acids. In some embodiments, the disclosure provides methods of "microbiome" analysis comprising a 16s rDNA amplification and sequencing approach, wherein a library of bacterial nucleic acid in a sample is prepared.

Nucleic Acid Purification and Sequencing

In additional embodiments, the disclosure provides methods of double stranded cDNA (ds-cDNA) synthesis from nucleic acid isolated and purified from a sample. Accordingly, embodiments of the disclosure provide methods of purifying the nucleic acid from a sample, or from a fraction of a sample, wherein the purified nucleic acid is suitable for first strand cDNA synthesis templated on RNA isolated from the sample.

In some embodiments, the disclosure provides a method of nucleic acid purification suitable for subsequent ds-cDNA synthesis. In certain embodiments, the methods of the disclosure comprise nucleic acid purification by methods known in the art. For example, the nucleic acid purification of the disclosure can employ a commercially available kit for nucleic acid purification. In some embodiments, a commercially available kit for nucleic acid purification comprises a Trizol LS, Zymo Viral RNA, or Qiagen Minelute kit.

The methods of the disclosure further provide methods of first strand DNA synthesis templated from nucleic acids isolated and purified from a sample. In some embodiments, first-strand synthesis reactions use a SuperScript IV Reverse Transcriptase first-strand synthesis kit (ThermoFisher™, Cat. No. 18090010). In some embodiments, first strand DNA synthesis according the present methods uses random hexamers at a concentration matching that used for ds-cDNA synthesis via the Invitrogen ds-cDNA synthesis kit (see, e.g., SuperScript® III First-Strand Synthesis System, ThermoFisher™, Cat. No. 18080051). In some cases, first strand synthesis according to the present method uses primers wherein the random portion comprises 9, 12 or 15 nucleotides. In other embodiments of the disclosure, the first strand synthesis uses the 5'-blocked primers, such as Illumina barcode primers, again at a concentration matching that used for the other cDNA synthesis reactions (see, e.g., SuperScript® III First-Strand Synthesis System, ThermoFisher™, Cat. No. 18080051).

In an exemplary embodiment, first strand cDNA synthesis is performed using random hexamers, wherein the sample or fraction thereof is denatured for 10 minutes and 80° C. in the presence of random hexamers to denature dsDNA and dsRNA present in the sample and subsequently cooled to allow hexamers to anneal. In an alternative exemplary embodiment, first strand cDNA synthesis is performed using random hexamers, wherein the sample or fraction thereof is denatured for 3 minutes and 95° C. prior to primer addition to denature dsDNA and dsRNA present in the sample. In embodiments, the first strand cDNA synthesis reaction mixture is further comprised of a first strand reaction buffer, a reducing agent (e.g. dithiothreitol), an enzyme or enzyme combination that inhibits RNAses (e.g. RNAse Inhibitor, or RNasein.), and a reverse transcriptase (SuperScript IV Reverse Transcriptase first-strand synthesis kit (ThermoFisher™, Cat. No. 18090010). The reaction mixture is vortexed gently and centrifuged to return volume to bottom of the reaction tube. The reaction is then incubated, sequentially, at 23° C. for 10 min, 50° C. for 10 min, and 80° C. for 10 min. After incubation the reaction is transferred to ice.

In another aspect, the methods of the disclosure provide second strand synthesis for preparation of double stranded DNA. Accordingly, the disclosure provides methods of making a library of double stranded DNA molecules comprising sequences complementary to the nucleic acids present in the sample. In some embodiments, second strand synthesis is accomplished using a second strand synthesis module (e.g. Roche®, cDNA Synthesis System, Cat. No. 11117831001; PrimeScript™ Double Strand cDNA Synthesis Kit, Clonetech, Cat. No. 6111A; NEBNext®, New England Biolabs, Cat. No. E6111S), with an intervening AMPURE cleanup to remove first-round primer.

Embodiments of the present disclosure further provide purification of the double strand cDNA produced according to the method, and described above. In embodiments, the double stranded DNA prepared from a sample is purified using commercially available reagents, such as Ampure XP beads (Beckman Coulter Genomics, Cat. No. A63881), or column-based DNA purification kits, for example, the Clean and Concentrator kits from Zymo Research (Cat. No. D4003).

In some embodiments, the disclosure provides alternative methods of making nucleic acid libraries using low amounts of starting materials. Thus, the present disclosure obviates the requirement for an amplification step prior to library preparation that can introduce bias in the sample, and distort or mask the frequency of pathogen derived nucleic acid in a sample.

In some embodiments the disclosure provides a method of making libraries from a sample, or a fraction thereof, using commercially available library preparation methods. For example, a "Tagmentation" reaction is provided wherein nucleic acids prepared from a sample according to methods of the disclosure are processed using commercially available Nextera® technology. In embodiments, the nucleic acids isolated from a sample according to the disclosure are processed directly using Nextera® index primers according to the methods supplied by the manufacturer (Illumina, Cat. No. FC-131-1024).

In some embodiments, the nucleic acids prepared by the Tagmentation method are purified after the reaction. For example, in some embodiments, the nucleic acids are purified using commercially available reagents, such as Ampure XP beads (Beckman Coulter Genomics, Cat. No. A63881).

Bioinformatics Methods and Systems for Metagenomic Analysis

In embodiments of the disclosed methods, nucleic acid sequence information can be extracted from a sample and read into a computing system. Thereafter, in silico translation of nucleotide sequences into amino acid sequences can be performed. In embodiments, the nucleic acid sequence information is processed by "de novo assembly" to assemble nucleic acid sequences in a sample into longer contiguous sequences ("contigs"), wherein said contigs are translated into amino acids for comparison to a curated database. Accordingly, methods of the disclosure can be improved by such de novo assembly because contiguous sequences are longer than individual sequences, and thus the probability of a "match" to the database is higher. The amino acid sequences are then compared to a custom, curated database of reference amino acid sequences.

The curated database is selectively culled from the protein sequences in a large reference database, which can be any comprehensive, integrated, non-redundant, well-annotated set of reference sequences including genomic, transcription, and/or protein information. In an example embodiment, the National Institutes of Health (NIH) RefSeq database can be used as the reference database. The reference database is curated to remove duplications, identified as sequences that exhibit greater than a threshold sequence identity (e.g., similarity >88%), in keeping with the field's consensus that 85-88% identity is the approximate cutoff between 'similar' and 'same'.

The focus on amino acid sequences can reduce the time per comparison (using current computing power) from 30 minutes to hours, as for nucleotide sequences (even in a curated database), to 2-5 minutes per comparison using the curated database. As an example, methods and systems described herein can provide microbe identification with a 60-90 fold speed-up over conventional methods. As such, methods and systems described herein can be more efficient than nucleotide-based counterparts and also can detect novel microbes with very low similarity to known microbes (e.g. down to approximately 20% nucleotide similarity).

Furthermore, present methods and systems can be applied to data generated from any number of sequencing platforms and can be used for a variety of purposes. Namely, embodiments described herein can be utilized for veterinary and human diagnostics, soil analysis, or the identification of contaminants for food safety, water safety, and quality control purposes during industrial processes.

Example embodiments described herein can provide a bioinformatic "pipeline" for quickly and efficiently processing metagenomic data for the identification of microbes, including viruses, bacteria, and other microorganisms with DNA or RNA genomes.

EXAMPLES

The Examples that follow are illustrative of specific embodiments disclosed herein and various uses thereof. They are set forth for explanatory purposes only and are not to be taken as limiting.

Example 1: General Method for Preparing a Library of an Unbiased Population of Microbe Nucleic Acid from a Sample Sample Preparation.

Tissue preparations using bovine placenta samples were cut on dry ice into 1×2×2 mm sections. Tissue preparations using porcine lung were cut into sections of the same dimensions.

Samples of horse serum spiked with virus were prepared by obtaining horse serum from a commercial source and adding a mixture of cultured viruses, to simulate an infected sample. In this case the viruses contain genomes of single stranded RNA, double stranded RNA, single stranded DNA and double stranded DNA, to represent the major classes of viral genomes in nature.

In some embodiments of the disclosure, the samples were homogenized according to the following method. Tissue samples ≤25 mg) or virus-spiked serum were transferred to a chilled MoBio, Inc. bead-beating tube (2.0 mL, 2.38 mm metal beads, catalog number 13117-50) along with 600 μL THE buffer (50 mM Tris-HCl, 150 mM NaCl, 1 mM EDTA, pH 7.4) per 25 mg tissue according to manufacturer's protocol. The bead-beating tubes were placed in a bead-beating tube rack (stored at −20° C.) and 3 cycles were performed of 20 seconds each at maximum speed (Biospec products, MiniBeadbeater), with a 15 second rest between cycles.

Virus Concentration.

All transfers/centrifugations in the following were performed on ice or under refrigeration. Eppendorf protein LoBind tubes were used for all but the DNA/RNA elution step.

Step 1: Tissue sample or serum (following bead beating) was transferred to a 1.5 mL Eppendorf® LoBind microcentrifuge (protein) tube (Eppendorf®, Cat. No. 022431081). Optionally, 5 μL of a $10^{-4}$ dilution of bacteriophage MS2 (roughly 5,000 to 25,000 genome equivalents) was added to the sample prior to all treatments.

Step 2: The sample was centrifuged at $10\times10^3$ g for 10 minutes. The supernatant was carefully transferred to a clean 1.5 mL Eppendorf tube without disturbing the pellet. The pellet was frozen at −20° C. or −80° C. and saved for subsequent processing.

Step 3 (optional): If sample volume was greater than 200 μL, viruses were concentrated by 2-hour centrifugation at maximum speed ($2.5\times10^4$ g, 4° C.) in a microcentrifuge. Following centrifugation, all but ~170 μL of supernatant was carefully removed. If the sample volume was less than 200 μl, this step was skipped, because the entire volume of the sample was carried forward.

Step 3: First supernatant (from Step 2) was under laid with 150 μL of 20% sucrose, constituted in TNE (Tris/NaCl/EDTA buffer). Virus was concentrated by 3-hour centrifugation at maximum speed ($2.5\times10^4$ g 25,000×g, 4° C.) in a microcentrifuge. Following centrifugation, all supernatant was carefully removed.

The second supernatant was carefully removed and a volume of 85 μl was retained.

Nuclease Treatment and Nucleic Acid Extraction.

The free (non-encapsidated) DNA and RNA was removed from the second pellet via nuclease cocktail treatment. A nuclease mix (see, e.g., Table 1) was added to the virus pellets and incubated at 37° C. for 30 min with shaking.

TABLE 1

Nuclease mix for digestion of non-encapsidated nucleic acid.

| | Stock conc. | Volume (μL) per 200 μL Sample | Final concentration |
|---|---|---|---|
| Serum or water | NA | 170 | NA |
| Turbo DNase (Ambion) | 2 U/μL | 8 | 0.08 U/μl |
| RiboShredder (Epicentre) | 1 U/μL | 1 | 0.005 U/μl |
| RNase A (Epicentre) | 5000 μg/mL | 1 | 25 ng/μl |
| Turbo DNase buffer | 10x | 20 | 1x |

Immediately following nuclease treatment, one volume (e.g., 200 μL) of 2× DNA-RNA Shield was added (Zymo Research, Cat. No. R1100). The viral nucleic acids were extracted from the first or second pellet, or the first or second supernatants, using a Qiagen viral MinElute kit, excluding the "recommended" wash step. (Quiagen, Cat. No 57704). The nucleic acids were eluted in total volume of 24 μL.

Double-Stranded cDNA Synthesis

First and second strand synthesis for RNA+DNA virus detection was performed using 10 μL of eluted DNA/RNA (e.g. as prepared in example 1, supra).

Eluted nucleic acid was transferred into a PCR tube, 2 μl random hexamers (25 pmol addition; stock was 50 ng/μL=12.6 μM), and 1.0 μl dNTPs (10 mM) were added. The solution was vortexed and collected in a microcentrifuge, incubated at 80° C. for 10 min, and immediately placed on ice for 2 min. To detect double-stranded RNA viruses, nucleic acid was optionally denatured for 3 min @ 95° C., then returned to ice.

With tubes on ice, 7 μL of the following master mix (SSIV first-strand RXN) was added:

| | 8.2 RXNs |
|---|---|
| 4.0 μl 5x First-Strand reaction buffer | 32.8 μL |
| 1.0 μl 100 mM DTT | 8.2 μL |
| 1.0 μl RNaseOUT | 8.2 μL |
| 1.0 μl SuperScript IV RT | 8.2 μL |

The components were mixed by gentle vortexing and collected by brief microcentrifugation. Each tube was incubated at 23° C. for 10 min and then at 50° C. for 10 min, 80° C. for 10 min and immediately thereafter transferred to ice.

60.0 μL of the following mix was added to each 20 μl sample (NEB $2^{nd}$-strnd RXN):

| | 8.2 RXNs |
|---|---|
| 48 μl UltraClean PCR water | 393.6 μL |
| 8.0 μl 10x Second-Strand reaction buffer | 65.6 μL |
| 4.0 μl Enzyme mix | 32.8 μL |

The components were mixed by gentle vortexing and collected by brief microcentrifugation. Each tube was incubated at 16° C. for 3.0 h, without a heated lid.

Purification of Double-Stranded cDNA.

In certain embodiments, the DNA generated during first and second strand synthesis was purified using Ampure XP beads (Beckman Coulter Genomics cat #: A63881) according to the manufacturer's instructions. Briefly, 140 μl of Ampure XP beads (1.75×) was added, the components were mixed by gentle vortexing for 5 s at medium speed and incubated at room temperature for 10 min. Each tube was then placed on a magnetic particle concentrator (MPC) for 8 min. The supernatant was removed and the beads washed twice with 150 μl of fresh 80% ethanol. The ethanol was removed and discarded and the pellet air-dried at room temperature for 4 min. 21 μl EB-buffer was added to each tube while the tube was still on MPC to elute the DNA. Once the beads had pelleted, 20 μl of supernatant was transferred to a strip-tube or 96-well plate.

Volume-reduction purification using Ampure XP beads: 35 μl of Ampure XP beads (1.75×) was added to each tube and the components gently vortexed for 5 s at med speed and then incubated at room temperature for 5 min. Each tube was placed on a magnetic particle concentrator (MPC) for 5 min. The supernatant was removed and the beads washed twice with 120 μl of fresh 80% ethanol. The ethanol was removed and discarded and the pellet air-dried at room temperature for 3 min. 5.5 μl (serum) or 6.5 μl (tissue) EB-buffer (10 mM Tris, pH 8.5) was added to each tube while the tubes remained on MPC to elute the DNA. When the beads had pelleted, 5-6 μl of supernatant was transferred to a new thermocycler-compatible 96-well plate or strip tube.

The purified DNA was quantified according to methods known in the art. In exemplary embodiments, tissue samples and new sample types were quantified using the Qubit™ fluourometric quantitation system (ThermoFischer, Cat. Nos. Q33217, Q33216).

Tagmentation.

Exemplary embodiments of the disclosure employed a Tagmentation reaction of the entire purified DNA sample according to manufacturer protocols (Nextera® XT, Illumina® Cat No. FC-121-1031).

The following components were assembled on ice:

| Reagent | 1 reaction |
|---|---|
| Sample DNA (≤1 ng total input) | 5 μl |
| 2x TD buffer (stock Tagment DNA buffer) | 10 μl |
| Amplion Tagment Mix (ATM) | |
| Tissue samples: ATM | 5 μl |
| Serum samples: ATM | 2.0 μl |
| 1x TD buffer (diluted stock) | 3.0 μl |
| | 20 μl |

The components were mixed briefly by vortexing, and incubated at 55° C. for 5 minutes (using a heated lid) and then cooled to 10° C. Once the samples reached 10° C., 5 μl NT buffer (RT) (Neutralize Tagment buffer) were immediately added, gently pipetted up and down 5 times and then incubated for 5 min at RT.

Selecting Nextera® XT index primers (Illumina®, Cat. No. FC-131-1024): A unique combination of index primers was selected for each sample, by entering the chosen primers into a MiSeq sample sheet according to manufacturer protocols to ensure a "valid" combination.

Limited cycle PCR (Nextera XT index primers): the following reaction components were assembled at room temperature:

25 μl recovered DNA Fragment Library;
15 μl NPM mix (Nextera PCR Master mix);
5 μl index 1 (i7) XT;
5 μl index 2 (i5) XT;

In a total reaction volume of 50 μL. The components were gently mixed via pipetting.

The samples were cycled in a thermocycler under the following conditions:

| | |
|---|---|
| 72° C. for 3 minutes | |
| 95° C. for 30 seconds | |
| 95° C. for 10 seconds | |
| 55° C. for 30 seconds | 14x for standard, 1 ng; 15x, tissue*; 17x, serum |
| 72° C. for 30 seconds | |
| 72° C. for 5 minutes | |
| Hold at 10° C. | |

*If the tissue sample cDNA input was less than 1 ng

"With-Bead" Library Cleanup and Size Selection.

The DNA from the Tagmentation reaction was purified using Ampure XP beads as follows. 27 μl of Ampure XP beads (0.54×) were added to each 50 μl reaction mixture, mixed via pipetting and incubated at room temperature for 5 min. Each tube was then placed on a magnetic particle concentrator (MPC) for 3 min. The supernatant was removed and discarded and the beads washed twice with 150 μl of 80% ethanol. The ethanol was then removes and discarded and the pellet air dried at RT for 2.5 min. 77 μl of TB (10 mM Tris, pH 8.5) was added to each tube while remaining on MPC. The beads were resuspended in each tube by pipetting up and down about ten times and incubated for 5 minutes at room temperature. The sample was then processed for size-selection purification as described below.

Size-selection purification the DNA using Ampure XP beads: 50 μl of Ampure XP beads (0.65×) was added to the 77 μl DNA-bead mixture, mixed by pipetting and incubated at room temperature for 5 min. Each tube was then placed on a magnetic particle concentrator (MPC) for 5 min. After this incubation the supernatant was removed and discarded and the beads washed twice with 150 μl of 80% ethanol. The ethanol was then removed and discarded and the pellet air dried at room temperature for 2.5 min. 11 μl of TB (10 mM Tris, pH 8.5) was added while the tube remained on the MPC, and thereafter the tube was removed and the contents mixed by pipetting up & down ten times to resuspend the beads. The resuspended mixture was incubated at room temperature for 5 minutes and then place back on the MPC for 3 min to bind the beads, with the supernatant being transferred to a PCR plate/strip tube.

The concentration of the nucleic acid mixture was determined by Qubit and the fragment distribution thereof was determined using a Agilent Bioanalyzer according to manufacturer protocols.

The size-selected DNA from the Tagmentation reaction was sequenced according to known methods, following manufacturer protocols. For example, the DNA from the Tagmentation reaction was sequenced following the protocols of the Illumina MiSeq instrument. Other sequencing platforms were used in alternative exemplary embodiments (e.g. Ion Torrent, PacBio, Oxford Nanopore).

Example 2: Serial Centrifugation, and Centrifugation Through a Density Medium, Enrich Biological Samples for Viruses and Increase the Sensitivity of Virus Detection Using Metagenomic Methods Two exemplary aspects of the disclosure were determined experimentally: centrifugation at high speed and centrifugation through a density medium. The methods were assessed for the ability to enrich for viruses from a starting population comprising heterogeneous nucleic acids, including host nucleic acid, thus enhancing detection of those viruses.

Preparing a Viral Horse Serum Bioreagent for Method Validation.

The methods of the disclosure described herein were applied to commercial horse serum "spiked" with a collection of cultured viruses. Specifically, 150 μL of horse serum was spiked with 20 μL of the virus mixture described in Table 2. This horse serum "bioreagent" was created for evaluation of the method for detecting viruses in cell-free fluids, such as serum, plasma, urine, cerebro-spinal fluid, water, etc.

TABLE 2

Description of viruses spiked into commercial horse serum to create a bioreagent for testing the ability of centrifugation at high speed and centrifugation through a density medium to enrich biological samples for viruses.

| Virus[1] | Stock titer | Stock Addition | Genome copies per 20 μL |
|---|---|---|---|
| BAdV-1 | Stock = $2.9 \times 10^7$ g.c./μL (qPCR) | 80 μL of $10^{-2}$ | $2.97 \times 10^5$ |
| PRD-1 | $3.4 \times 10^6$ g.c./μL stock (qPCR) | 10 μL (undiluted) | $4.25 \times 10^5$ |
| AAV | Unknown | Unknown | Unknown |
| Simian TTV | Unknown | Unknown | Unknown |
| MS2 | ~$5 \times 10^7$ g.c./μL (pos. to $10^{-6}$ dilution, cPCR) | 10 μL of $10^{-1}$ | $6.25 \times 10^5$ |
| SIV-239 | $2.24 \times 10^3$ g.c./μL (qPCR) | 1000 μL (serum) | $2.80 \times 10^4$ |
| EqPgV | Unknown | 150 μL, per sample | Unknown |
| NPHV | Unknown | 150 μL, per sample | Unknown |
| Eq Parvo | Unknown | 150 μL, per sample | Unknown |

TABLE 2-continued

Description of viruses spiked into commercial horse serum to create a bioreagent for testing the ability of centrifugation at high speed and centrifugation through a density medium to enrich biological samples for viruses.

| Virus[1] | Stock titer | Stock Addition | Genome copies per 20 μL |
|---|---|---|---|
| GBV-C | $4.7 \times 10^2$ g.c./μL | 500 μL | $2.94 \times 10^3$ |
| SHFVkrc-1 | $1.1 \times 10^4$ g.c./μL | | $6.88 \times 10^4$ |
| SHFVkrc-2 | $2.7 \times 10^3$ g.c./μL | | $1.69 \times 10^4$ |

[1]Viruses were obtained from commercial sources or from collaborating laboratories.

Serial Centrifugation, and Centrifugation Through a Density Medium.

The resulting "bioreagent" (horse serum spiked with viruses) was centrifuged for 10 minutes at 10,000×g, and the resulting supernatant was removed and subjected to two conditions prior to nucleic acid extraction: (1) no centrifugation (negative control) (designated "no cent" in Table 3), and (2) centrifugation at 25,000×g for 3 hours at 4° C. ("cent" in Table 3). All samples were then processed according to the remainder of the protocol described in Example 1, supra.

Table 3 presents the results of these experiments evaluating the effects of centrifugation on virus detection in horse serum bioreagent. Values presented are means of 2-6 trials. Centrifugation at 25,000×g for 3 hours increased viral detection for all viruses, and up to an order of magnitude for some viruses, when starting with a liquid sample (serum).

TABLE 3

Sequence reads per million total reads mapping to each of 10 viruses spiked into commercial horse serum.[1]

| | Viral sequence reads mapped per 1,000,000 total sequence reads | | | | | | | | |
|---|---|---|---|---|---|---|---|---|---|
| Treatment | SIV-239 | PRD-1 | BAdV-1 | SHFVkrc-2 | SHFVkrc-1 | GBV-C | EqPgV | MS2 | NPHV |
| 1 (no cent) | 21 | 50459 | 4282 | 350 | 325 | 248 | 38 | 8390 | 38 |
| 2 (cent) | 213 | 203991 | 11312 | 1062 | 1040 | 256 | 367 | 10319 | 388 |

[1]Not all viruses present in the horse serum bioreagent were assayed; therefore results represent a subset of viruses spiked in the original sample.

In addition, the impact of conducting the second centrifugation step through a 20% sucrose solution was determined for samples derived from tissue. A sample of bovine placenta tissue (approximately 10 mg) was spiked with 20 μl of the horse serum bioreagent described above. The tissue was homogenized and centrifuged for 10 minutes at 10,000×g to generate a first supernatant and a first pellet. The resulting supernatant was removed and subjected to two treatments prior to nucleic acid extraction: (1) centrifugation at 25,000×g for 3 hours at 4° C. (designated "no sucr." in Table 4), and (2) centrifugation at 25,000×g for 3 hours at 4° C., through 150 μl of 20% sucrose solution underlain beneath the first supernatant ("sucr." in Table 4). All samples were then processed according to the remainder of the protocol described in Example 1, supra.

Results were evaluated as the proportion of sequence reads of the spiked viruses (or that subset of them that were detected), under the hypothesis that the experimental conditions described above would enrich for viruses and lead to higher proportions of viral reads. Table 4 presents the results of the experiment evaluating the effects of centrifugation through a sucrose density medium on virus detection in horse serum bioreagent. Values presented are means of 2-6 trials. Centrifugation through a sucrose solution enabled detection of viruses that otherwise would not have been detected, when starting with solid tissue.

TABLE 4

Sequence reads per million total reads mapping to viruses detected in bovine placenta spiked with the bioreagent.

| | Viral sequence reads mapped per 1,000,000 total sequence reads | | | | | | | | |
|---|---|---|---|---|---|---|---|---|---|
| Treatment | SIV-239 | PRD-1 | BAdV-1 | SHFVkrc-2 | SHFVkrc-1 | GBV-C | EqPgV | MS2 | NPHV |
| 1 (no sucr) | No viruses detected | | | | | | | | |
| 2 (sucr) | 8 | 581 | 61 | 317 | 310 | 0 | 0 | 328 | 0 |

[1] Not all viruses present in the horse serum bioreagent were assayed; therefore results represent a subset of viruses spiked in the original sample.

Example 3: Nuclease Digestion of Biological Samples After High-Speed Centrifugation Nuclease Digestion of Biological Samples After High-Speed Centrifugation to Pellet Viruses Increased the Sensitivity of Virus Detection Using Metagenomic Methods.

To evaluate the effectiveness of nuclease digestion to enrich a biological sample for viral nucleic acid, the protocol in Example 2, supra, was modified with the addition of a nuclease digestion step. In particular, conditions for applying nuclease digestion of the second pellet after serial centrifugation were investigated. Because viral nucleic acid was protected from digestion by the viral particle (the virion), treating the virus pellet with a mix of nucleases was used to remove free nucleic acid ("contaminating" nucleic acid from the host and other sources) under conditions where viral nucleic acid was "spared."

A "cocktail" of nucleases was added to the second pellet isolated according to the methods in Example 2, supra. The nuclease cocktail was comprised of:

| Component | Stock concentration | Volume (μL) added per 200 μL digestion reaction |
|---|---|---|
| Serum or water | NA | 170 |
| Turbo DNase (Ambion) | 2 U/μL | 8 |

-continued

| Component | Stock concentration | Volume (μL) added per 200 μL digestion reaction |
|---|---|---|
| RiboShredder (Epicentre) | 1 U/μL | 4 |
| RNase A (Epicentre) | 5000 μg/mL | 1 |
| Turbo DNase buffer | 10x | 20 |

The second pellet was either mock treated (designated "no nucl" in Table 5), or exposed to the nuclease cocktail ("nucl" in Table 5), and incubated at 37° C. for 30 minutes with shaking. The resulting samples were then processed according to the remainder of the protocol described in Example 1, supra. The data are presented in Table 5. Nuclease treatment increased viral detection for all viruses, and over an order of magnitude for some viruses, when starting with a liquid sample (serum). Moreover, the results showed an improvement in viral genome length sequenced in the two experiments described above (704 nucleotides more coverage of the average viral genome) and of the depth of the viral genome covered (1756 read increase in the number of reads mapping to the average viral genome).

TABLE 5

Sequence reads per million total reads mapping to each of 10 viruses spiked into commercial horse serum.[1]

| | Viral sequence reads mapped per 1,000,000 total sequence reads | | | | | | | |
|---|---|---|---|---|---|---|---|---|
| Treatment | SIV-239 | PRD-1 | BAdV-1 | SHFVkrc-2 | SHFVkrc-1 | EqPgV | MS2 | NPHV |
| 1 (no nucl) | 94 | 1471 | 681 | 6778 | 7230 | 48 | 19298 | 141 |
| 2 (nucl) | 960 | 36901 | 1282 | 63531 | 65687 | 670 | 319160 | 1517 |

[1]Not all viruses present in the horse serum bioreagent were assayed; therefor results represent a subset of viruses spiked in the original sample.

Immediate Addition of DNA/RNA Shield™ Reagent Following Nuclease Digestion Increased the Sensitivity of Virus Detection Using Metagenomic Methods.

To further optimize viral nucleic acid enrichment when using a nuclease treatment step, the impact of immediate cessation of the nuclease digestion by addition of a nuclease inactivator was also tested. Nuclease treated samples described above were either mock treated, or exposed to 1 volume of 2× DNA/RNA Shield™ immediately after nuclease digestion according to the manufacturer's protocol. The resulting samples were then processed according to the remainder of the protocol described in Example 1, supra. The data are presented in Table 6. Addition of DNA/RNA Shield™ increased viral detection for all but one viruses (PRD-1). (Table 6. ) In addition, an improvement in viral genome length sequenced in the two experiments described above (886 nucleotides more coverage of the average viral genome) and of the depth of the viral genome covered (25 read increase in the number of reads mapping to the average viral genome) was observed. (Table 6. )

TABLE 6

Sequence reads per million total reads mapping to each of 10 viruses spiked into commercial horse serum.[1]

| | Viral sequence reads mapped per 1,000,000 total sequence reads | | | | | | | |
|---|---|---|---|---|---|---|---|---|
| Treatment | SIV-239 | PRD-1 | BAdV-1 | SHFVkrc-2 | SHFVkrc-1 | EqPgV | MS2 | NPHV |
| 1 (no Shield) | 56 | 1082 | 546 | 3359 | 4282 | 70 | 7778 | 163 |
| 2 (Shield) | 152 | 880 | 661 | 5077 | 6212 | 84 | 11796 | 208 |

[1]Not all viruses present in the horse serum bioreagent were assayed; therefore results represent a subset of viruses spiked in the original sample.

Example 4: Efficient Pooling of Libraries for Multiplexed Sequencing on an Illumina MiSeq Instrument Produced High-Quality Data for Viral Detection Libraries prepared according to the methods described above were pooled using a spreadsheet distributed by Illumina Inc., with several modifications to simplify pooling. The modifications comprise new algorithms allowing the user to input a desired percent of the instrument's sequencing capacity to dedicate to each sample. This was calculated as follows:

Volume of library to add=[(target pool concentration×desired percentage of the cartridge)/100×(pool volume/concentration of the sample)]

Additionally, the modifications optimized the final concentration of sodium hydroxide (NaOH) in the pooled library to be loaded into the sequencing cartridge. Pooled DNA libraries must be denatured in the presence of 0.1 N NaOH and then diluted so that the final concentration of NaOH in the sample added to the instrument cartridge was less than 0.01 N. If the NaOH concentration was too high, the sequencing run could fail. However, low-input samples, those with cDNA starting concentrations below the detection limit of the nucleic acid quantification system (e.g. the Qubit fluorometer (Thermo Fisher Scientific, Waltham MA), which has a limit of detection of 0.05 ng/μL), often had very low DNA concentrations following library preparation that require a larger volume of sample to be pooled into the library. This large volume requires increased NaOH addition for denaturation, and could lead to a final library concentration that was too high if default protocols for library pooling prior to sequencing was followed. Instead, the methods disclosed herein permit the user to choose a higher NaOH concentration to denature the pooled samples (reducing the overall volume and the total amount of NaOH added to the sample). In addition, a standard acid-base calculation was included, indicating whether neutralization of excess NaOH in the final library was required (i.e., for the concentration to be below 0.01 N NaOH), and, if so, how much 0.5 N hydrochloric acid (HCL) to add to the library.

The following algorithm operationalizes this logic:

If the NaOH concentration of the 20 picomolar library was greater than:

[(0.001 normal×the volume of the final library)/the volume of 20 picomolar library added to the final library], then the volume of 0.5 normal HCl to be added to the 20 picomolar library prior to dilution equals [(0.0008−0.001)×1000/0.5] microliters.

The method for library pooling described above was applied using database software (e.g. Microsoft Excel, or other suitable software). The methods can be further modified to calculate, e.g., the number of reads desired for any given sample, rather than the percentage of the sequencing cartridge used.

Table 7 shows statistics associated with the 16 completed runs on an Illumina MiSeq instrument. The percentage of clusters passing filter (% PF), average reads with quality scores above Q30 (AVG % above Q30), and gigabase pairs (Gbp, an indicator of yield) were good to excellent. This success was due in part to careful optimization of the library pooling strategy.

TABLE 7

Run statistics showing success of optimized library pooling strategy.

| Cycles | Yield | % PF | Avg % above Q30 |
|---|---|---|---|
| 301 \| 301 | 12.04 Gbp | 0.9424 | 0.7176 |
| 301 \| 301 | 12.36 Gbp | 0.7543 | 0.6449 |
| 301 \| 301 | 10.65 Gbp | 0.9584 | 0.5946 |
| 301 \| 301 | 10.84 Gbp | 0.9449 | 0.6926 |
| 276 \| 276 | 16.00 Gbp | 0.8593 | 0.6515 |
| 301 \| 301 | 17.47 Gbp | 0.8842 | 0.6143 |
| 301 \| 301 | 9.57 Gbp | 0.5897 | 0.4298 |
| 301 \| 301 | 15.71 Gbp | 0.8553 | 0.6156 |
| 301 \| 301 | 17.68 Gbp | 0.8516 | 0.6601 |
| 300 \| 275 | 18.87 Gbp | 0.8298 | 0.6185 |
| 280 \| 280 | 17.36 Gbp | 0.8518 | 0.723 |
| 76 \| 76 | 4.98 Gbp | 0.8231 | 0.9119 |
| 280 \| 260 | 16.18 Gbp | 0.8975 | 0.7036 |
| 280 \| 260 | 13.19 Gbp | 0.7125 | 0.5186 |
| 281 \| 261 | 13.11 Gbp | 0.9355 | 0.8464 |
| 260 \| 250 | 13.96 Gbp | 0.9118 | 0.7988 |
| 301 \| 301 | 17.96 Gbp | 0.9071 | 0.7601 |
| 301 \| 281 | 17.33 Gbp | 0.9075 | 0.7099 |

Example 5: Method for Preparing an Unbiased Population of Non-Viral Agents, Such as Bacteria and Eukaryotic Pathogens, by Analysis of the "Microbiome" and the "MitoBiome"

Established microbiome methods, and MitoBiome methods disclosed herein, were applied to the first pellet fraction in the methods disclosed supra. Notably, the present methods were also applicable to a first or second supernatant, which retain some amount of microbial or parasitic nucleic acid.

An experiment was conducted to recover mitochondrial DNA sequences from fecal samples known to contain parasite eggs. In the present example, the fecal samples were from humans, but this method was designed to work with any sample from any source.

Figure 3:
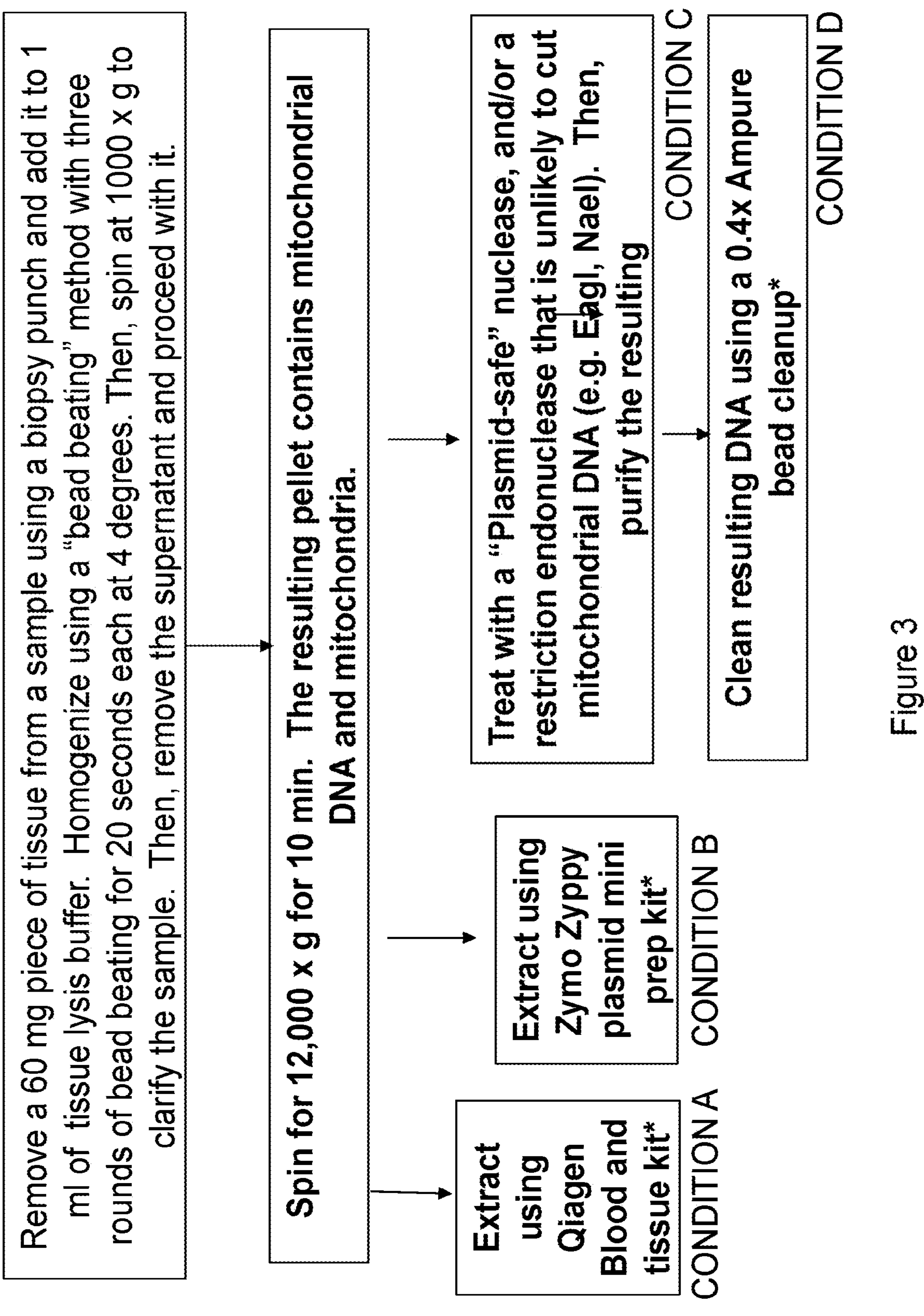
FIG. 3 shows a schematic for preparation of samples for Microbiome and "MitoBiome" analysis from samples prepared according to methods of the disclosure. Methods were performed per manufacturer's instructions where indicated. Conditions referenced in the figure correspond to Example 5, infra.

Two human fecal samples were collected (1 mL each) and suspended 1:1 in RNAlater. Samples were aliquoted into 6 300 μL portions, supplement with 900 μL of Hanks buffer (to dilute RNAlater), subject to bead beating (max speed, 3 cycles, 20 s each), clarified (10,000 g, 10 min), and supernatants combined to ensure homogeneity. Supernatant were distributed equally (~150 mg feces equivalent) to each of the following conditions, corresponding to the "options" recited in the flow chart in FIG. 3.

Condition A: crude pellet extracted with Qiagen DNeasy Blood and tissue kit as per manufacturer instructions (Qiagen, Hilden, Germany, Cat. No. 69504).

Condition B: crude pellet extracted using Zymo Zyppy plasmid miniprep kit as per manufacturer instructions (Zymo, Irvine, CA, Cat. No. D4036).

Condition C: Nuclease treated with "plasmid safe" nuclease, such as Epicentre (Madison, WI) Plasmid-Safe™ ATP-Dependent DNase (catalog number E3101K), as per manufacturer instructions. Plasmid safe nuclease treatment could be performed with other enzymes or enzyme combinations, such as the restriction enzyme EagI (New England Biolabs, Ipswich, MA, catalog number R0190S) as per manufacturer instructions, under the rationale that EagI is a rare cutting enzyme, chosen because it has a single cut site in human mitochondrial DNA, and inferred rare cut sites in other mitochondrial sequences. Other restriction enzymes (e.g. NaeI) could be used instead or in addition.

Condition D: reaction purified with 0.4× Agencourt AMPure XP beads (Agencourt, Beverly, MA, catalog number A63882) as described, supra.

Nucleic acid from each condition was eluted to the volumes specified by the manufacturer, and quantified via Qubit using the Quant-iT™ PicoGreen® dsDNA Assay Kit (Invotrogen, Carlsbad, California, catalog number P7589). 1 ng purified nucleic acid was used as input for Nextera® XT Tagmentation kit (Illumina, San Diego, California, catalog number FC-131-1096) according to the method described in Example 1, supra. The results are presented in Table 8. Results demonstrate that mtDNA reads were recovered from most conditions, without the use of PCR or other primer-based means to amplify mtDNA.

TABLE 8

Mitochonrial DNA (mtDNA) sequences recovered from human fecal samples under various conditions. Each condition was designed to examine whether mtDNA can be selectively purified/enriched and sequenced using "unbiased" metagenomic methods, and whether mtDNA from eukaryotic microbes can be selectively purified/enriched relative to host mtDNA.

| Sample/ condition | Total Reads | Human mtDNA reads | Human mtDNA reads (normalized to 1 million reads) | Condition Tested |
|---|---|---|---|---|
| 1a | 237726 | 10 | 42.1 | Extraction of DNA from crude homogenate: no enrichment for mtDNA. |
| 1b | 190166 | 4 | 21.0 | DNA isolated from crude homogenate with plasmid isolation kit to enrich for circular mtDNA over linear genomic DNA |
| 1c | 186415 | 2 | 10.7 | Ampure cleanup with size selection to remove small DNA fragments and thus enrich for larger mtDNA |
| 1d | 266944 | 14 | 52.4 | Enzymatic digestion with a rare cutting enzyme (Eagl ) chosen to preferentially cut host mtDNA and thus enrich for parasite mtDNA. |
| 1e | 371348 | 13 | 35.0 | Enzymatic digestion with another rare cutting restriction enzyme (Nael ) chosen to preferentially cut host mtDNA over parasite mtDNA and thus enrich for parasite mtDNA. |
| 2a | 1539995 | 30 | 19.5 | Extraction of DNA from crude homogenate: no enrichment for mtDNA. |
| 2b | 1790366 | 4 | 2.2 | DNA isolated from crude homogenate with plasmid isolation kit to enrich for circular mtDNA over linear genomic DNA |

TABLE 8-continued

Mitochonrial DNA (mtDNA) sequences recovered from human fecal samples under various conditions. Each condition was designed to examine whether mtDNA can be selectively purified/enriched and sequenced using "unbiased" metagenomic methods, and whether mtDNA from eukaryotic microbes can be selectively purified/enriched relative to host mtDNA.

| Sample/ condition | Total Reads | Human mtDNA reads | Human mtDNA reads (normalized to 1 million reads) | Condition Tested |
|---|---|---|---|---|
| 2c | 285690 | 2 | 7.0 | Ampure cleanup with size selection to remove small DNA fragments and thus enrich for larger mtDNA |
| 2d | 482060 | 0 | 0.0 | Enzymatic digestion with a rare cutting restriction enzyme (Eagl ) chosen to preferentially cut host mtDNA and thus enrich for parasite mtDNA. |
| 2e | 482755 | 2 | 4.1 | Enzymatic digestion with another rare cutting restriction enzyme (Nael ) chosen to preferentially cut host mtDNA over parasite mtDNA and thus enrich for parasite mtDNA. |

Example 6: Application of the Disclosed Methods to 5 Completely Sequenced Reference Viruses Representing the Full Spectrum of Virus Genome Composition Five completely sequenced reference viruses (Table 9) were spiked into fetal bovine serum (FBS) lacking microbial contaminants (clean FBS, confirmed by qPCR, and externally validated by another lab (Table 10)). The viral spiked FBS test reagents were split into 11 samples, prepared as described, supra, resulting in a libraries of nucleic acid for subsequent sequencing steps. The samples were sequenced at two dilutions: 6 samples were diluted to 100× the limit of detection (LOD) (measured by real time quantitative PCR), and 5 samples were diluted to 1× LOD.

TABLE 9

Sequenced reference viruses tested in Example 6

| Virus | Family | Genome | Genome size (nt) | Accession # |
|---|---|---|---|---|
| Parvovirus ("Parvo") | Parvoviridae | ssDNA | 5394 | KT148961 |
| Respiratory syncytial virus ("RSV") | Paramyxoviridae | ssRNA (−) | 15140 | NC_001989 |
| Bovine viral diarrhea virus ("BVDV") | Flaviviridae | ssRNA (+) | 12573 | NC_001461 |
| Bluetongue virus ("BTV") | Reoviridae | dsRNA (10 segments) | 19185 | JQ972831-JQ972840 |
| Bovine herpesvirus 1 ("IBRV") | Herpesviridae | dsDNA | 135301 | AJ004801 |

TABLE 10 qPCR evaluation of titered virus spiked into clean FBS

| Virus | 100x LOD Ct value | 1x LOD Ct value |
|---|---|---|
| IBR | 28.1 | 34.2 |
| BTV | 31.7 | 39.0 |
| BVDV | 29.8 | 36.1 |
| RSV | 30.4 | 36.1 |
| Parvo | 32.0 | ≥40 |

Figure 4A:
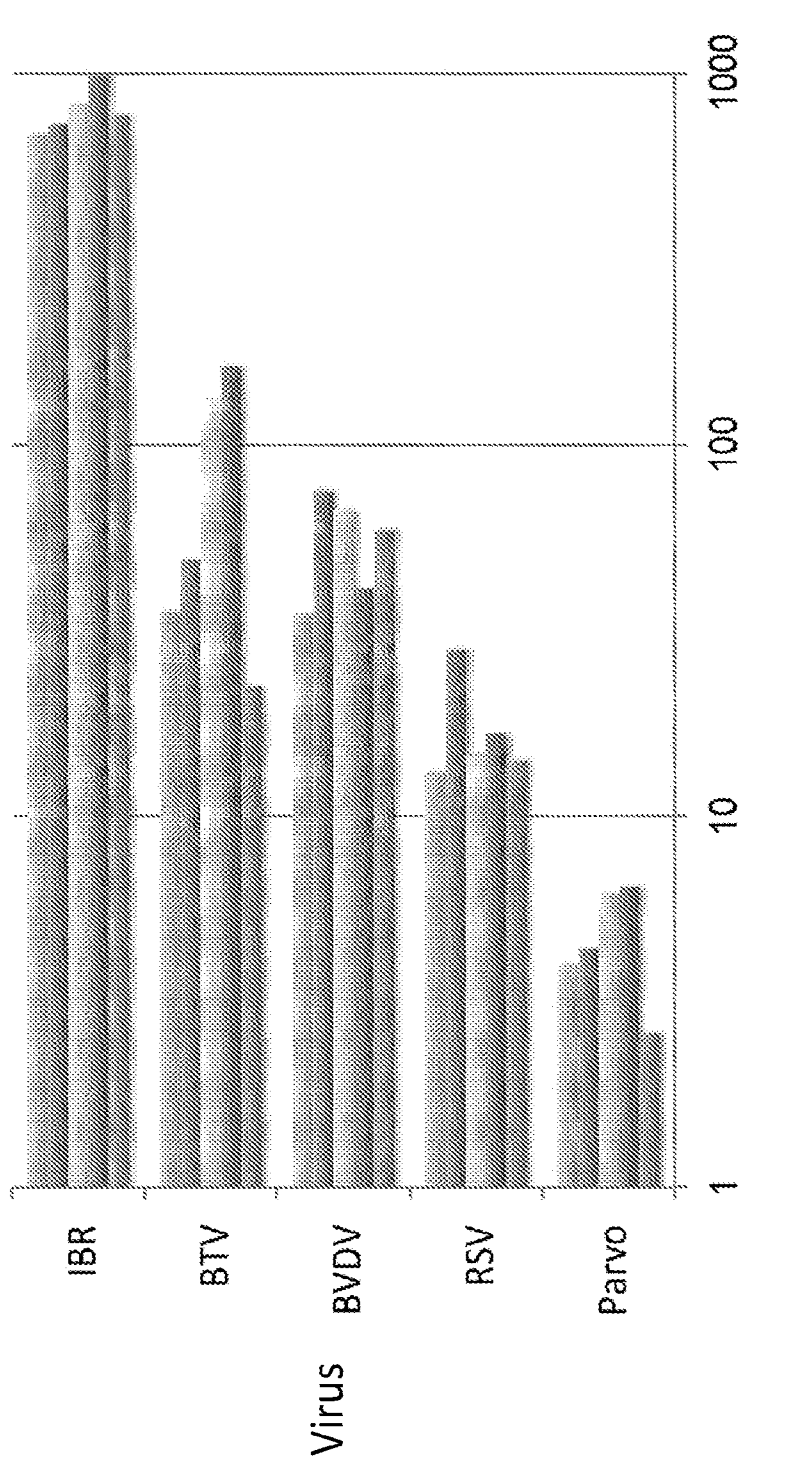
FIG. 4A shows the log transformed results of five replicates of virus spiked fetal bovine serum (FBS) samples at 1× limit of quantitative PCR (qPCR) detection for each of five viruses (IBR=Infectious bovine rhinotracheaitis virus; BTF=bluetongue virus; BVDV=Bovine viral diarrhea virus; RSV=Respiratory syncytial virus; Parvo=bovine parvovirus).
Figure 4B:
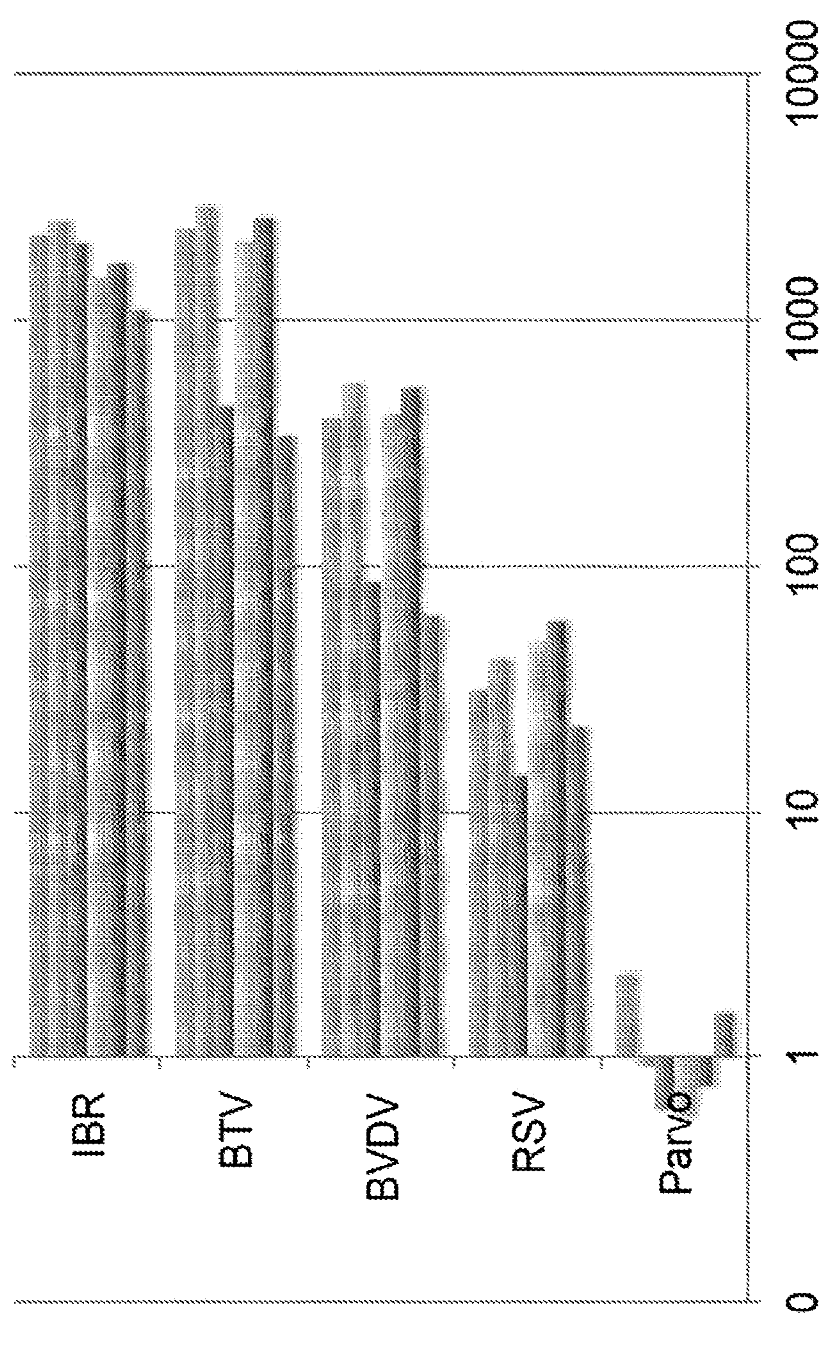
FIG. 4B shows the log transformed results of six replicates of virus spiked FBS samples at 100× limit of qPCR detection for each of the same five viruses.
Figure 5:
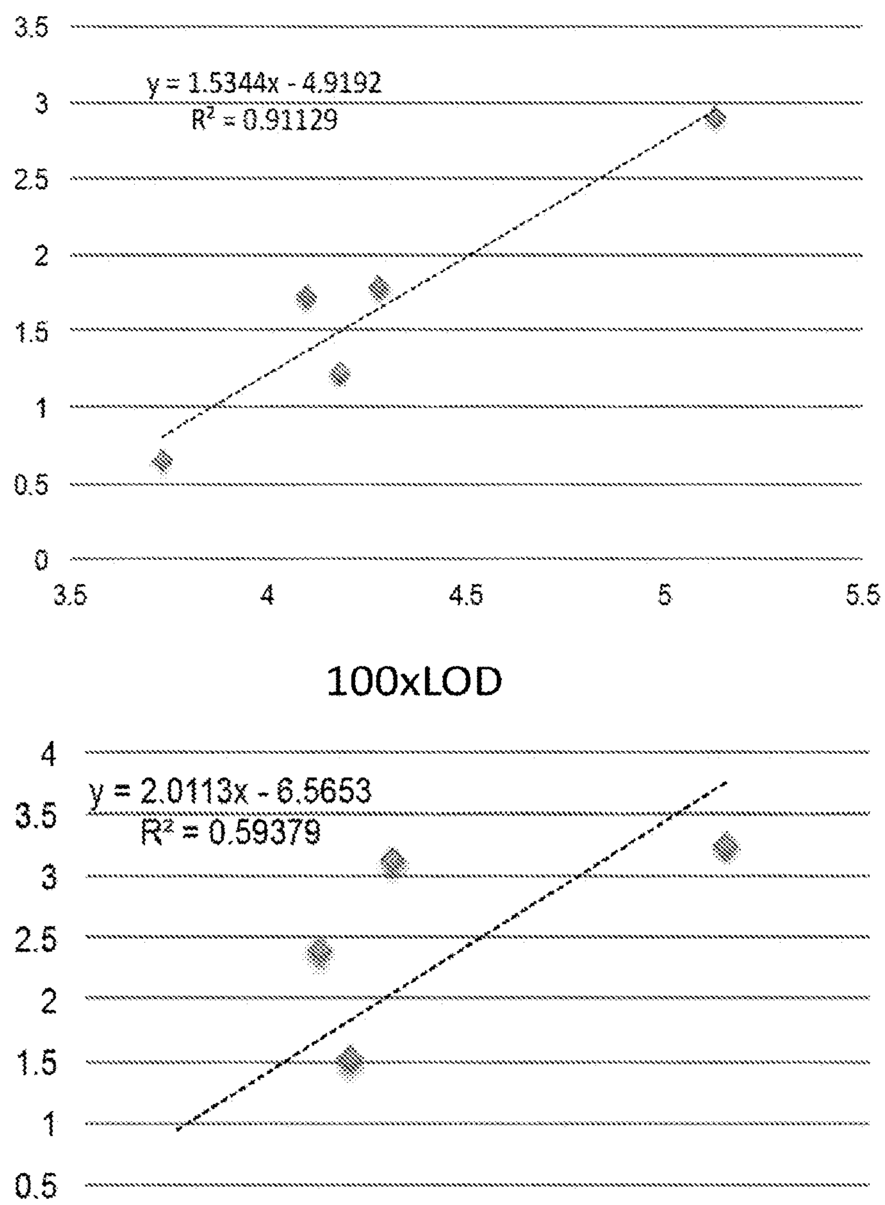
FIG. 5 shows the log transformed read depth of the samples in FIGS. 4A and 4B plotted as a function of genome size.

Libraries were sequenced on an Illumina MiSeq with v2 150×150 paired-end chemistry (concentrations normalized by Bioanalyzer and Qubit). The resulting reads were trimmed at Q30 ≤50 n.t. Trimmed reads were mapped to full genomes of each virus at length fraction 0.7 and similarity fraction 0.8 (default parameters). The run statistics and results of the run are shown in Table 11 and FIGS. 4A and 4B (total reads: 39189534; % PF: 95.6306; CV:0.3891% reads per sample range: 3.98-11.97). The method detected all viruses in all replicates at both concentrations (100× LOD and 1× LOD).The read depth of the data correlated with viral genome size (FIG. 5)

TABLE 11

Run statistics showing success using viral spiked FBS test reagents.

| Cycles | Yield | % PF | Avg % above Q30 |
|---|---|---|---|
| 318 | 5.75 Gbp | 0.99 | 0.91 |

Example 7: Application of the Disclosed Methods to Previously Developed Reference Material for Adventitious Virus Detection The methods of the disclosure were applied to a previously developed reference material (the "Mee et al. reference material") developed for adventitious virus detection (Mee, E. T., M. D. Preston, P. D. Minor, S. Schepelmann and C. S. S. Participants (2016), *Vaccine* 34: 2035-2043). Briefly, the Mee et al. reference material comprises 25 viruses, with some at uncertain concentrations and some with no full genome sequences available, spiked into 10 mM Tris with 2% FBS (for full description of the Mee et al. reference material, see id).

Two aliquots of the Mee et al. reference material were processed according to the methods described supra. Libraries were sequenced on an Illumina MiSeq with v2 150×150 paired-end chemistry (concentrations normalized by Bioanalyzer and Qubit). The resulting reads were trimmed at Q30 ≤50 n.t. Trimmed reads were assembled and queried against viral sequences downloaded from GenBank (LF 0.5, SF 0.7) (actual viral sequences in the published reference material are not known, so a random sequence of each virus from GenBank was selected, favoring sequences in the RefSeq database). The run statistics and results of each run are shown in Tables 12 and 13 (total reads: 39189534; % PF: 95.6306; CV:0.3891% reads per sample range: 3.98-11.97).

TABLE 12

Run statistics showing success using the Mee et al. viral spiked FBS test reagents.

| Cycles | Yield | % PF | Avg % above Q30 |
|---|---|---|---|
| 318 \| 318 | 5.75 Gbp | 0.99 | 0.9148 |

TABLE 13

Results using Mee et al. reference material (trimmed reads mapped at LF 0.5, SF 0.7)

| Virus | Aliquot 1 (2,170,885 reads) | Aliquot 2 (1,978,784 reads) |
|---|---|---|
| Adenovirus 2 | 4106 | 5544 |
| Adenovirus 41 | 133 | 126 |
| Human herpesvirus 1 | 1274 | 616 |
| Human herpesvirus 2 | 2235 | 2439 |
| Human herpesvirus 3 (VZV) | 13723 | 12707 |
| Human herpesvirus 4 (EBV) | 3389 | 3240 |
| Human herpesvirus 5 (CMV) | 27193 | 29361 |
| Rotavirus A (all segments) | 297834 | 226091 |
| Astrovirus | 82 | 23 |
| Norovirus GI | 4 | 1 |
| Norovirus GII | 7 | 0 |
| Sapovirus C12 | 81 | 30 |
| Coronavirus 229E | 20 | 16 |
| Coxsackievirus B4 | 54 | 14 |
| Rhinovirus A39 | 13 | 9 |
| Parechovirus 3 | 9181 | 1012 |
| Influenza A virus H1N1 (all segs) | 436 | 262 |
| Influenza A virus H3N2 (all segs) | 2035 | 1638 |
| Influenza B virus (all segments) | 47 | 103 |
| Metapneumovirus A | 321 | 84 |
| Parainfluenzavirus 1 | 305 | 25 |
| Parainfluenzavirus 2 | 55626 | 6137 |
| Parainfluenzavirus 3 | 14 | 8 |
| Parainfluenzavirus 4 | 555 | 257 |
| Respiratory syncytial virus A2 | 7 | 8 |

Summary read statistics:

Total reads: 39189534; % PF: 95.6306; CV:0.3891

- Aliquot 1: 6.7861% of reads on the run
  - 2,487,272 reads before trimming
  - 2,170,885 reads after trimming at ≥Q30, 50 bases
  - 137.4 bases average length after trimming
- Aliquot 2: 6.0827% of reads on the run
  - 2,229,482 reads before trimming
  - 1,978,784 reads after trimming at ≥Q30, 50 bases
  - 144.7 bases average length after trimming The results using the Mee et al. reference material showed target read depth ($2\times10^6$) that was nearly perfect. All viruses were detected in aliquot 1, and all but norovirus GII were detected in aliquot 2. The performance of the method therefore matched or exceeded the performance reported in the Mee et al reference by 16 laboratories participating in the study.

Bioinformatics Methods Examples

Figure 6:
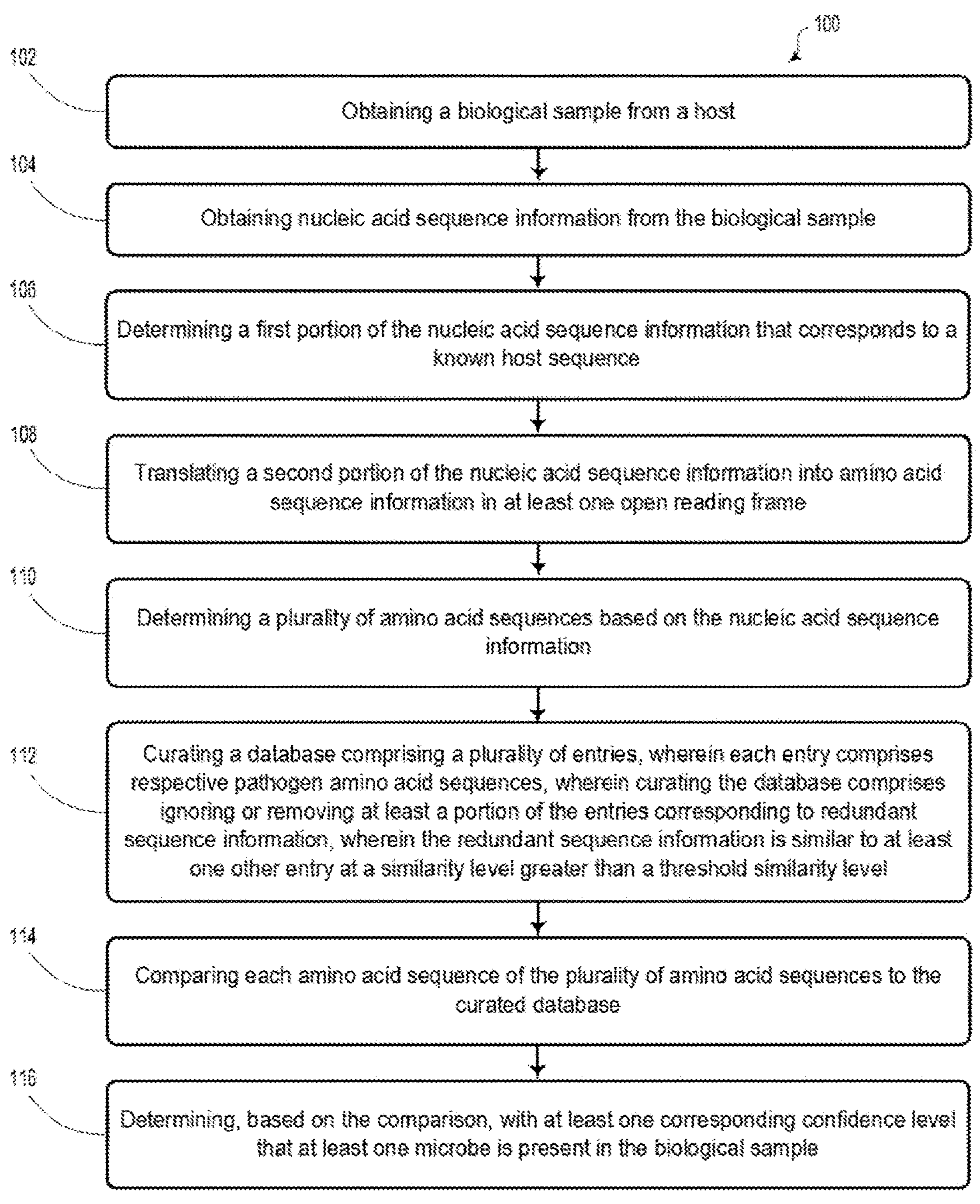
FIG. 6 is a flowchart illustrating a method according to an example embodiment.

FIG. 6 is a flowchart illustrating a method 100 according to an example embodiment. The method 100 includes blocks that can be carried out in any order. Furthermore, various blocks can be added to or subtracted from method 100 within the intended scope of this disclosure. The method 100 can correspond to blocks that can be carried out using any or all of the devices and/or systems illustrated and described in reference to FIG. 7A, 7B, or 8. In some embodiments, computing device 230 of system 200 can be configured to carry out at least some of the blocks disclosed herein.

Block 102 includes obtaining a biological sample from a host. In an example embodiment, the host can include a mammal, such as a primate (e.g., a human); however, other animal hosts are contemplated. Additionally or alternatively, plant or bacteria hosts are possible, as well as environmental samples (e.g. water, soil) and industrial samples (e.g. raw materials, finished products). Generally, hosts need only to contain, carry (e.g., transport), or act as media for nucleic acid sequence information. As such, a host can even include soil, air, or water.

Block 104 includes obtaining nucleic acid sequence information from the biological sample. In an example embodiment, the biological sample can include at least one of: water, soil, air, a tissue, a biological fluid, feces, or another product or byproduct from the host. In such a scenario, obtaining the nucleic acid sequence information can include obtaining the nucleic acid sequence information from the water, soil, air, tissue, biological fluid, feces, or another product or byproduct. In an example embodiment, obtaining the nucleic acid sequence information from the biological sample can include isolating nucleic acid from the biological sample so as to favor mitochondrial nucleic acid and disfavor other types of nucleic acid. Thereafter, the isolated nucleic acid can undergo an unbiased shotgun-sequencing method.

In an example embodiment, block 104 can include a tissue homogenizing step and a two-stage centrifugation step using a density medium during the second centrifugation. In an example embodiment, the centrifugation can provide a pellet. Block 104 can also include treating the pellet with a plurality of nucleases, which can selectively digest host nucleic acids, but not viral nucleic acids because they can be protected inside virus particles. Block 104 can additionally or alternatively include a process step after nuclease treatment to stop nuclease digestion quickly and to improve recovery of nucleic acid sequences, particularly from viruses. As an example, block 104 can include adding a DNA/RNA SHIELD treatment; however, other similar treatments are contemplated.

In some embodiments, obtaining nucleic acid sequence information from the biological sample can include double stranded cDNA synthesis. Additionally or alternatively, embodiments can include carrying out an unbiased polymerase chain reaction-free method.

In an example embodiment, the nucleic acid sequence information can be obtained from, in part, using a bioanalyzer tool, such as an Agilent 2100 bioanalyzer. The obtained nucleic acid sequence information can include one or more ribonucleic acids or deoxyribonucleic acids, e.g., RNA or DNA. The nucleic acid sequence information can include "coding" or "non-coding" information.

Block 106 includes determining a first portion of the nucleic acid sequence information that corresponds to a known host sequence. That is, the nucleic acid sequence information can be compared to a known host genome. For instance, if the biological sample is primate tissue, much of the nucleic acid sequence information can match a known genome of the primate. Sample sequence information that matches the known genome of the host, which can be termed the first portion of the nucleic acid sequence information, can be deleted, discounted, or ignored for the remainder of method 100.

In an example embodiment, determining a first portion of the nucleic acid sequence information can include carrying out a whole genome shotgun sequencing method; however, other sequencing and/or comparison methods are possible and contemplated herein.

The method 100 can optionally include removing, from the nucleic acid sequence information, the first portion of the nucleic acid sequence information so as to provide the second portion of the nucleic acid sequence information. In other words, where certain portions of the nucleic acid sequence information from the sample are determined to match a host sequence, that portion can be erased, deleted, moved, cut, or otherwise removed from the nucleic acid sequence information under consideration by method 100.

Block 108 includes translating a second portion of the nucleic acid sequence information into amino acid sequence information in at least one open reading frame. In an example embodiment, the second portion of the nucleic acid sequence information can be translated into amino acid sequence information via a transcription or translation tool. For example, such a tool can be configured to translate a DNA sequence into an RNA sequence. The tool can also be configured to translate the RNA sequence into a protein/amino acid sequence. In some embodiments, web-based nucleotide sequence translation software such as EMBOSS Sixpack can be utilized to perform the translation of block 108. In such a scenario, the nucleotide sequence information can be input into the translation software in a text-based FASTA format, which can represent each nucleotide of the sequence as a single-letter code. It is understood that other representations or formats are possible and contemplated herein.

Block 110 includes determining a plurality of amino acid sequences based on the nucleic acid sequence information. The amino acid sequences can include one or more long chains of peptides. In an example embodiment, the amino acid sequences can include proteins that extend between an N-terminal end containing free amino group and a C-terminal end containing a free carboxyl group.

Block 112 includes curating a reference database comprising a plurality of entries. Each entry includes a respective microbe amino acid sequence. In an example embodiment, the reference database can include Genbank, or a portion thereof, such as a RefSeq search group. Other reference databases are possible and contemplated herein.

Curating the reference database includes ignoring, discounting, and/or removing at least a portion of the entries corresponding to redundant sequence information. In an example embodiment, the redundant sequence information can be similar to at least one other entry at a similarity level greater than a threshold similarity level.

In an example embodiment, the block 112 can include iteratively mapping small sequences (e.g., <1000 amino acid residues) to larger sequences (e.g., >1000 amino acid residues) to remove small redundant sequences and saving "unmapped" reads, or matches to sequences in the reference database or the curated database. All of the unmapped reads can be collected and further culled to remove similar sequences at, for example, an 88% similarity level.

In some embodiments, the threshold similarity level is selected within a range between 90-95%; however, other threshold similarity levels are possible and contemplated. For example, the threshold similarity level could be between 80-99%. In an example embodiment, the threshold similarity level can be selected, for example, based on the host, a target microbe, a target set of microbes, sample quality, sample homogeneity, or other factors.

In the case of Genbank, the total number of viral nucleotide sequences as of August 2016 is approximately 2,024,000. Assuming 10 protein sequences per virus, there can be ~20 million potentially biologically-relevant protein sequences that can be extracted from these ~2 million nucleotide sequences (6 reading frames).

By applying the methods described herein, curating the reference database can result in a curated database with entries that relate to viral nucleotide sequences. In an example embodiment, the number of entries in the curated database can be reduced by between a ~72-270-fold in comparison to the number of entries in the reference database. In such embodiments, the fold reduction in the number of sequences can approximate the fold reduction in analysis time.

In some embodiments, an amino acid database can be determined based on the unmapped reads, or a subset thereof. For instance, the method can include finding open reading frames (ORFs) larger than 100 amino acid residues. The ORFs can be assigned to an entry in the amino acid database, retaining read name and region. Entries can include both small sequences, e.g., 50-1000 amino acid residues as well as large sequences, e.g., 1000-5000 amino acid residues. The entries in the amino acid database can be further culled based on overlapping ORFs. In an example embodiment, each ORF nucleotide sequence entry in the amino acid database can be translated to an ORF amino acid sequence.

The amino acid database can represent the curated database. The new amino acid database can be used as a curated reference database for a sequence search engine, such as BLASTx, RAPSearch, or RAPSearch2.

Although embodiments above relate to a viral pathogen database, other types of databases are possible. For example, block 110, or variations thereof, can be used to form a curated non-viral pathogen database. For example, a curated "MitoBiome" database can be formed from mitochondrial DNA sequences of known helminth, protozoan, apicomplexan, fungal or other types of organisms that contain mitochondria and mitochondrial DNA.

Block 114 includes comparing each amino acid sequence of the plurality of amino acid sequences to the curated database. In an example embodiment, comparing each amino acid sequence of the plurality of amino acid sequences to the curated database includes comparing at least one open reading frame (ORF) of each amino acid sequence to the curated database. In some embodiments, each of the six standard reading frames of each amino acid sequence can be compared to the curated database.

Block 116 includes determining, based on the comparison, with at least one corresponding confidence level that at least one microbe is present in the biological sample. That is, in an example embodiment, "hits" (matches to microbial protein sequences) from block 114 can be used as the basis for reconstructing the original nucleic acid sequence of a given microbe.

Determination of the at least one microbe and the corresponding confidence level could be determined based on querying all potential viral sequences (which is typically a many order-of-magnitude reduction from the original number of sequences obtained during the sequencing run) against the publically available comprehensive Genbank database. Such a method can reduce the number of "false positives" that are returned by the nucleotide and amino acid comparisons.

In some embodiments, prior to comparison with viral databases, some entries can be ignored or removed based on matching a host sequence (e.g., human genomic DNA), common bacterial sequences present in commercial reagents (the use of which is required to generate sequencing-ready DNA, e.g., biotech strains of *E. coli*), common false positive sequences (mostly viral "vector" sequences) and low-complexity sequences that might randomly match portions of a viral genome (e.g., AAAA . . . , GGGG . . . , CCCCC . . . , TTTT . . . , ATATAT . . . , AATTAATT . . . and so on).

These steps can ultimately result in reduced computational time by reducing the initial number of "false positive" reads that "resemble" viral sequences.

In some embodiments, the at least one microbe can include a eukaryotic parasite. Additionally or alternatively, the at least one microbe can include a bacterium, a virus, or a eukaryotic pathogen.

Bioinformatics System Examples

Figure 7A:
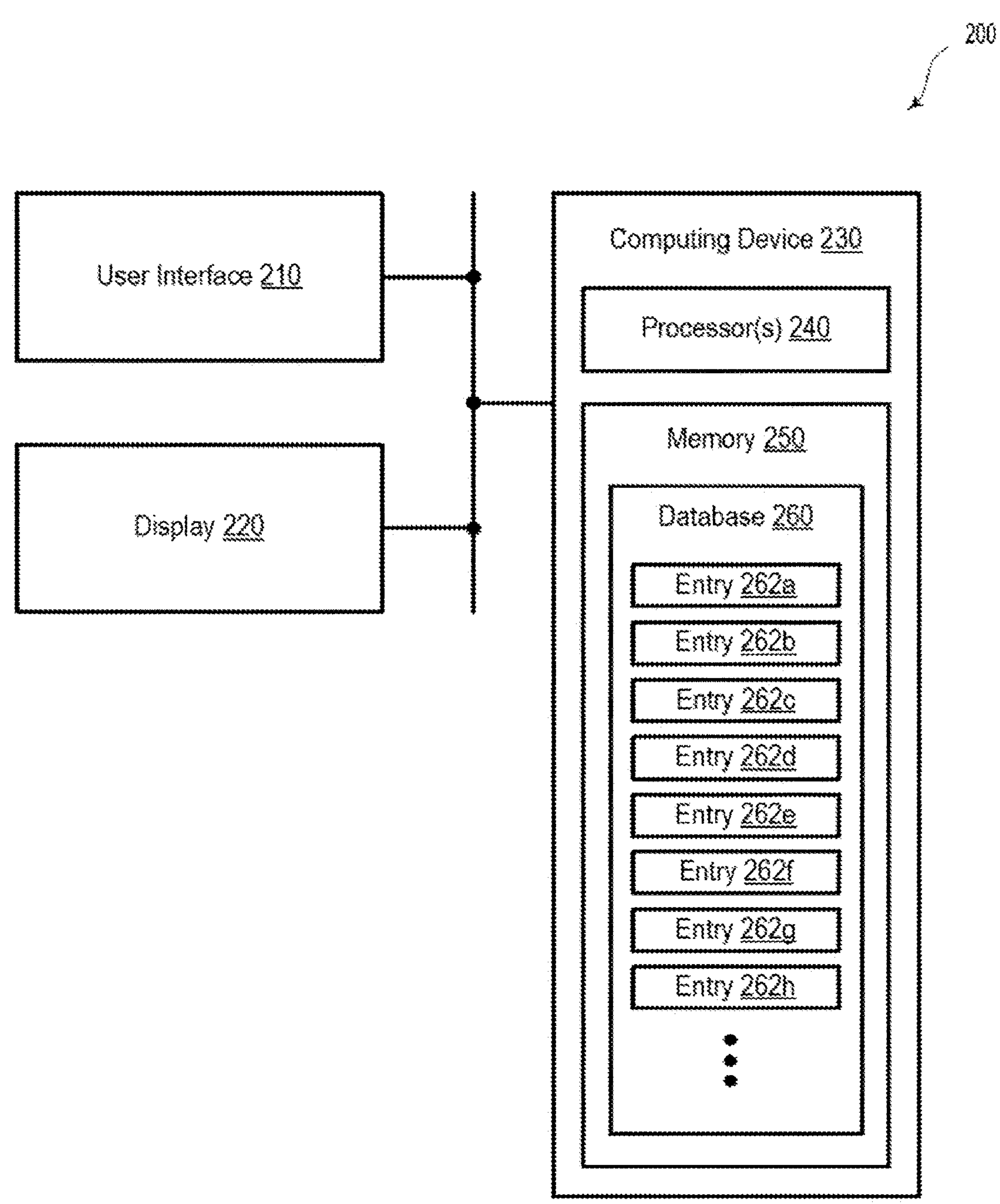
FIG. 7A is a block diagram of a system according to an example embodiment.

FIG. 7A is a block diagram of a system 200 according to an example embodiment. Namely, system 200 can include a user interface 210, a display 220, and a computing device 230. In an example embodiment, the system 200 can include one or more of: a desktop computer, a laptop, a tablet computer, a smartphone, or another type of computing device.

The user interface 210 can provide a way for a user to interact with the computing device 230. Namely, the user interface 210 can include hardware devices such as a keyboard, a mouse, a touchscreen, a touchpad, a controller, or another type of user interface device. Furthermore, the user interface 210 can include software and/or firmware configured to provide an interactive experience with a user of system 200. That is, the user can control at least some aspects of the system 200 via the user interface 210.

In an example embodiment, the computing device 230 can provide that user interface 210 that can be displayed, at least in part, on the display 220. In some cases, the user interface 210 can be displayed in icon and/or menu form on the display 220. Additionally or alternatively, user interface 210 can be displayed as one or more buttons, sliders, graphs, charts, or other images on the display 220.

The computing device 230 of system 200 can include one or more processors 240 (e.g., integrated circuits or central processing units (CPUs)) and a memory 250. For example, processor 240 can include a processor with multiple processing cores (e.g., 48 processing cores). In some embodiments, the computing device 230 can include a distributed computing system or a supercomputer. As an example, a plurality of processors 240 could be distributed among one or more geographic locations, such as can occur in a cloud-computing network. The computing device 230 can additionally or alternatively represent one or more elements of a client-server network. That is, a user can access a client terminal of the computing device 230, which can, in turn, communicate with one or more servers to carry out desired database searches and/or database curation steps.

Memory 250 could include any type of computing hardware configured to store information for use (or during or after use) by computing device 230. Memory 250 could include either or both volatile or non-volatile types of memory devices. For example, memory 250 could include a flash memory, a read-only memory (ROM), a programmable read-only memory (PROM), an erasable programmable read-only memory (EPROM), or an electrically erasable programmable read-only memory (EEPROM). Additionally or alternatively, memory 250 can include primary memory devices, such as dynamic random-access memory (DRAM), static random-access memory (SRAM), or CPU cache memory. Other types of memory devices are contemplated and possible.

In an example embodiment, a database 260 can be stored in the memory 250. Additionally or alternatively, a portion of the database 260 can be stored in the memory 250 at a given time. In such scenarios, the database 260 can include a plurality of entries 262*a-h*. Generally, each entry 262*a-h* can include a single reference sequence, which can be associated with a protein/amino acid sequence, a transcript, and/or an organism. In an example embodiment, each entry of the database 260 can include a respective microbe-specific amino acid sequence.

Processor 240 can execute instructions stored in memory 250. As such, computing device 230 can be operable to perform operations, some of which can involve other elements of system 200.

In an example embodiment, computing device 230 can receive nucleic acid sequence information. For example, the received nucleic acid sequence information can have been obtained from a biological sample (e.g., blood, feces, saliva, dirt, air, etc.). In such a scenario, the nucleic acid sequence information includes information encoded in ribonucleic acids (e.g., RNA) and/or information encoded in deoxyribonucleic acids (e.g., DNA). In an example embodiment, receiving the nucleic acid sequence information can include obtaining the sequence information from a biological sample. Such extraction of the sequence information from the biological sample can include isolating nucleic acid from the biological sample so as to favor mitochondrial nucleic acid and disfavor other types of nucleic acid and subjecting the isolated nucleic acid to an unbiased shotgun-sequencing method.

The computing device 230 can receive the sequence information in a variety of manners, such as via a communication interface. In an example embodiment, the sequence information can be transmitted from a DNA sequencing tool (e.g. a MiSeq or NextSeq instrument from Illumina Inc.) to the computing device 230 via a computing network. In some embodiments, the computing device 230 can be incorporated into a bioanalyzer tool.

The computing device 230 can also determine a first portion of the nucleic acid sequence information that corresponds to a known host sequence. Determining the first portion of the nucleic acid sequence information can include the computing device 230 and/or the processor 240 carrying out a whole genome shotgun sequencing method. Additionally or alternatively, determining the first portion of the nucleic acid sequence information can include comparing the nucleic acid sequence information to a known host genome sequence via Refseq, or another reference database.

The computing device 230 can translate a second portion of the nucleic acid sequence information into amino acid sequence information in at least one open reading frame. As described elsewhere herein, the translation of the nucleic acid sequence information into the amino acid sequence information can be performed via nucleotide-to-amino acid translation software.

The computing device 230 can determine a plurality of amino acid sequences based on the nucleic acid sequence information. In some embodiments, the computing device 230 can remove duplicate information from the nucleic acid sequence information so as to provide the second portion of the nucleic acid sequence information.

The computing device 230 can, with or without interaction with a user, curate the database. Curating the database can include ignoring, discounting, or removing at least a portion of the entries corresponding to redundant sequence information. The redundant sequence information can be similar to at least one other entry at a similarity level greater than a threshold similarity level. In an example embodiment, the threshold similarity level is between eighty-five and ninety-five percent (e.g., eighty-eight percent). However, other threshold similarity levels are contemplated. In some embodiments, the plurality of protein sequences of the curated database can be less than 5% of the number of entries of the reference database.

The computing device 230 can compare each amino acid sequence of the plurality of amino acid sequences to the curated database. Comparing each amino acid sequence of the plurality of amino acid sequences to the curated database includes comparing an open reading frame (ORF) of each amino acid sequence to the curated database.

The computing device 230 can determine, based on the comparison, with at least one corresponding confidence level that at least one microbe is present in the biological sample.

The computing device 230 can display, via the user interface 210 and/or the display 220, the identity of the at least one microbe and the at least one corresponding confidence level. In an example embodiment, the at least one microbe could be a eukaryotic parasite. In other embodiments, the at least one microbe can include a bacteria, a virus, and/or a eukaryotic pathogen.

Figure 7B:
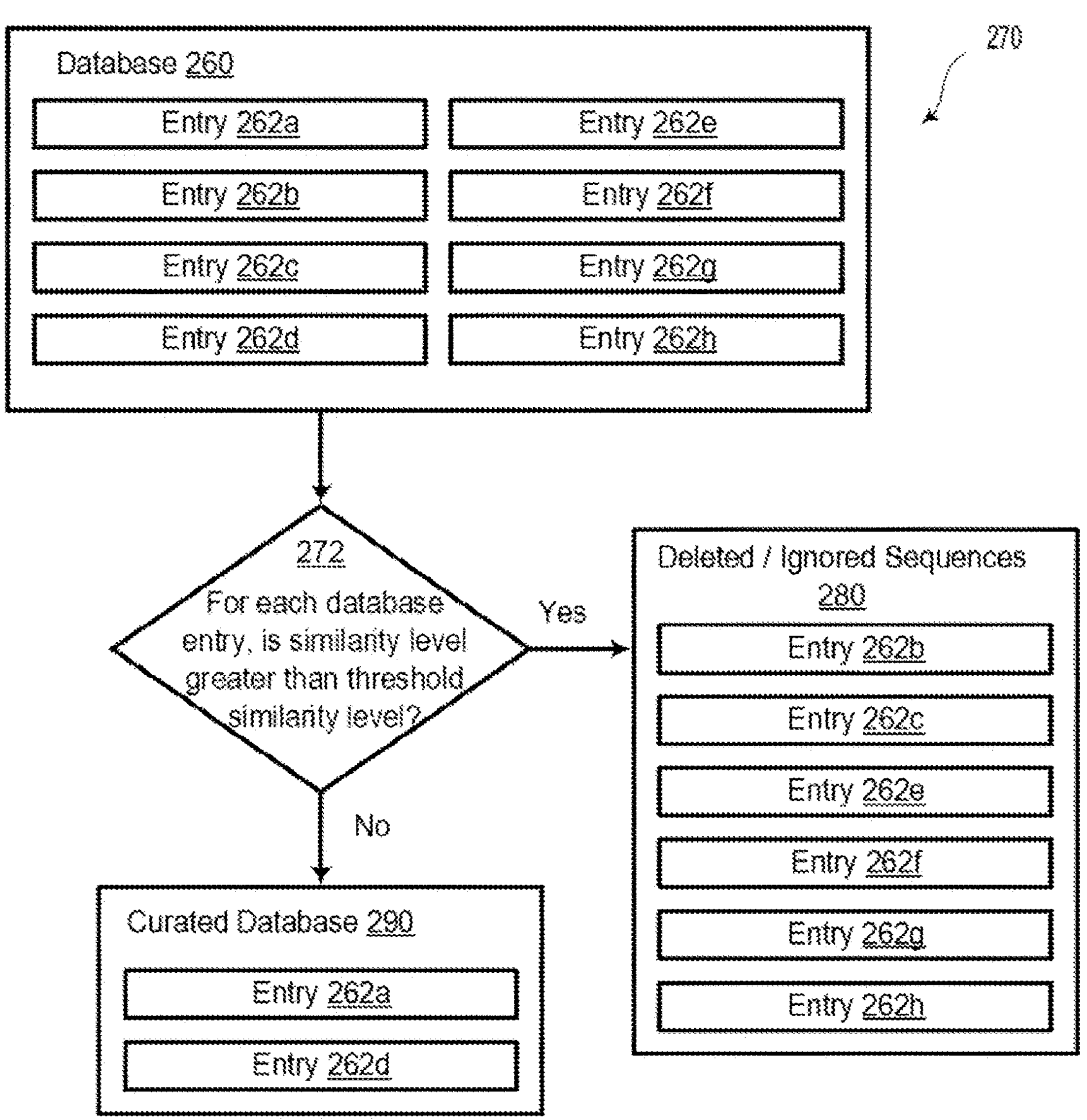
FIG. 7B is a block diagram illustrating database curation according to an example embodiment.

FIG. 7B is a block diagram illustrating database curation 270 according to an example embodiment. Database curation 270 can include the database 260, which can include a plurality of database entries (e.g., entries 262*a-h*). Each database entry can include at least an identifier and a known sequence of amino acids, which can relate to a protein (e.g., amino acid chain), an organism, and/or a transcript. The database entries can include other information about the sequence and/or include metadata (e.g., date of inclusion to the database, definition, version, keywords, host type, number of amino acids in the sequence, etc.). In an example embodiment, the database 260 can be a reference sequence database (e.g., Refseq), which can include millions of discrete sequence entries, or more.

Database curation 270 can include a determination 272, for each database entry, whether a given entry has a higher similarity level than a predetermined threshold similarity level. As described elsewhere herein, the threshold similarity level could be 90%; however, other threshold similarity levels are contemplated and possible. In an example embodiment, some or all elements of the database curation 270 can be performed by the computing device 230.

For example purposes only, entry 262*a* can include the amino acid sequence: MAFRLGGGLTGDAGIHR-LESLTGKTHYKDKYWYPDDYVYTTGNQKEEEKI-VAKLLLDPNA (SEQ ID NO: 1), where G is Glycine (Gly), P is Proline (Pro), A is Alanine (Ala), V is Valine (Val), L is Leucine (Leu), I is Isoleucine (Ile), M is Methionine (Met), C is Cysteine (Cys), F is Phenylalanine (Phe), Y is Tyrosine (Tyr), W is Tryptophan (Trp), H is Histidine (His), K is Lysine (Lys), R is Arginine (Arg), Q is Glutamine (Gln), N is Asparagine (Asn), E is Glutamic Acid (Glu), D is Aspartic Acid (Asp), S is Serine (Ser), and T is Threonine (Thr). Such a sequence can relate to, for example, the first six reading frames of a structural protein associated with bovine parvovirus-2. In an example embodiment, this sequence can be used as a reference sequence for comparison with other entries in the database 260.

Entries 262*b* and 262*c* can be compared to entry 262*a* across all reading frames. That is, the respective entries can be compared in an open reading frame (ORF) format. In such a scenario, entries 262*b* and 262*c* can be 98.3% similar to the sequence of entry 262*a*. As an example, entries 262*b* and 262*c* can include 59 out 60 identical bases (in the same order). If, as an example, the predetermined threshold similarity level is 90%, entries 262*b* and 262*c* can be deleted or ignored. For example, entries 262*b* and 262*c* can be moved to a set of deleted/ignored sequences 280.

Furthermore, entry 262*d* can include the amino acid sequence: melidrmllq NMTKQKPVGVEEPVYDQAG-NPLFGEIGAIHPQSTLKLPHNRGEREVPTNL (SEQ ID NO: 2), where G is Glycine (Gly), P is Proline (Pro), A is Alanine (Ala), V is Valine (Val), L is Leucine (Leu), I is Isoleucine (Ile), M is Methionine (Met), C is Cysteine (Cys), F is Phenylalanine (Phe), Y is Tyrosine (Tyr), W is Tryptophan (Trp), H is Histidine (His), K is Lysine (Lys), R is Arginine (Arg), Q is Glutamine (Gln), N is Asparagine (Asn), E is Glutamic Acid (Glu), D is Aspartic Acid (Asp), S is Serine (Ser), and T is Threonine (Thr). Such a sequence can relate to, for example, the first six reading frames of a non-structural protein associated with bovine viral diarrhea virus 1. In an example embodiment, entry 262*d* can have a similarity level of only 1.7% with entry 262*a*. That is, entry 262*d* can be substantially distinct from other entries previously considered and can be thus used as a reference sequence for comparison with other entries in the database 260.

Entries 262*e-h* can be compared to entry 262*d* across all reading frames. That is, the respective entries can be compared in an open reading frame (ORF) format. In the example above, entries 262*e* and 262*f* can be identical to entry 262*d* within the first six reading frames. As such, entries 262*e* and 262*f* can have a similarity level of 100% with respect to 262*d*. Accordingly, entries 262*e* and 262*f* can be moved to the set of deleted/ignored sequences 280. Entries 262*g* and 262*h* can both include two transpositions of amino acids in comparison with entry 262*d*. That is, entries 262*g* and 262*h* can share 56 out of 60 identical amino acids with entry 262*d*. As such, the similarity level could be determined to be 93.3%. As such, entries 262*g* and 262*h* can be moved to the set of deleted/ignored sequences 280.

In the example above, a curated database 290 can be provided that includes many-fold fewer entries while preserving statistically distinct genomic sequences.

Figure 8:
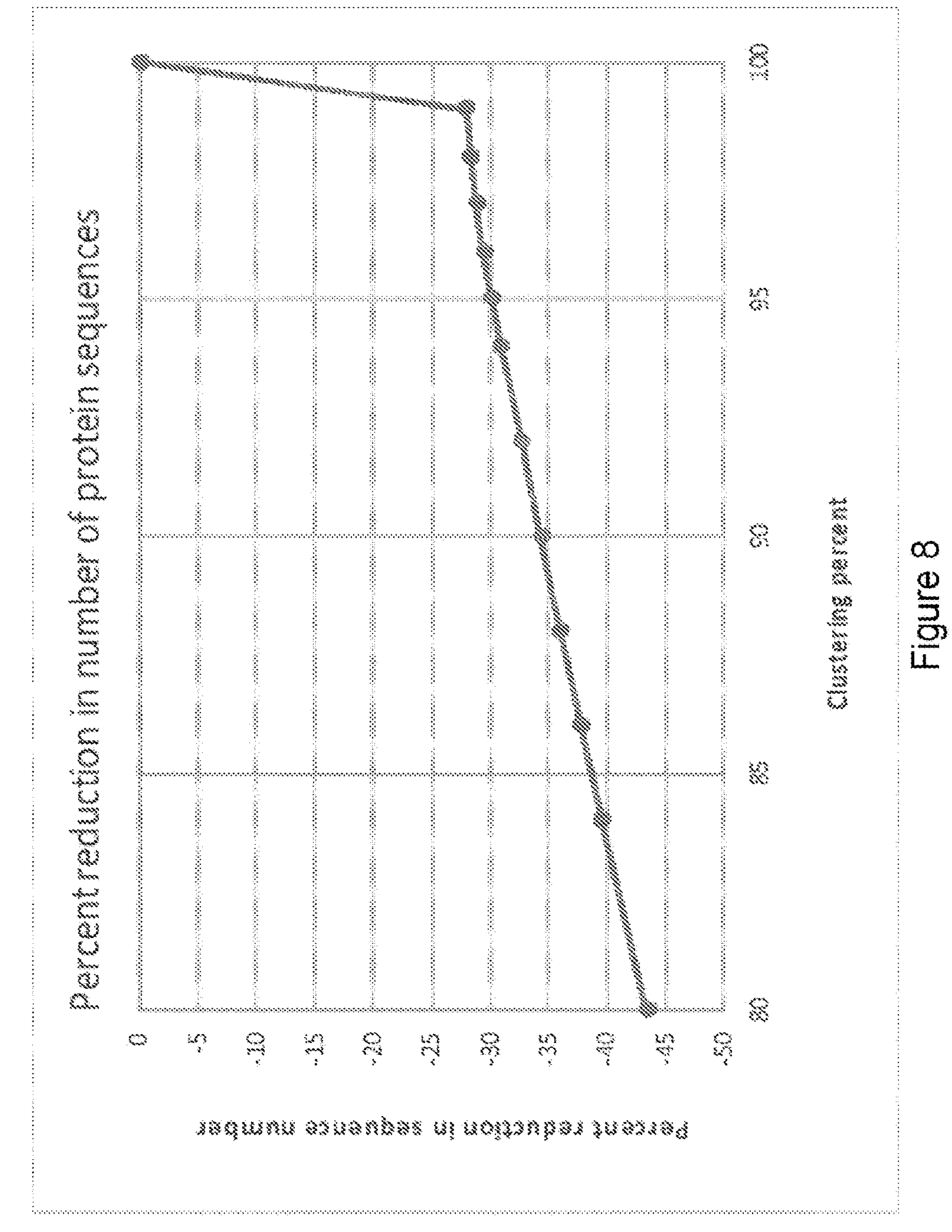
FIG. 8 shows a line graph of a percentage reduction in number of protein sequences versus clustering percent according to an example embodiment.

FIG. 8 illustrates a line graph 300 of a percentage reduction in number of amino acid sequences versus clustering percent according to an example embodiment. The initial number of sequences was 105493. Starting with viral nucleotide sequences that had been clustered into groups of 88% similarity or less (roughly corresponding a logical "species-level" classification), all open reading frames (ORFs) in the nucleotide sequence set were then found and extracted. The ORFs were translated into amino-acid sequences. As line graph 300 illustrates, to achieve significant database size reduction, amino acid sequences should be clustered using a low-percentage cutoff (e.g., 90%), which can result in significant loss of diagnostic resolution among similar microorganisms (in this case, viruses). However, the majority of reduction in the total number of database entries was gained by clustering at 99%, thus achieving efficiency gains (with regard to analysis time) and retaining diagnostic resolution.

Figure 9:
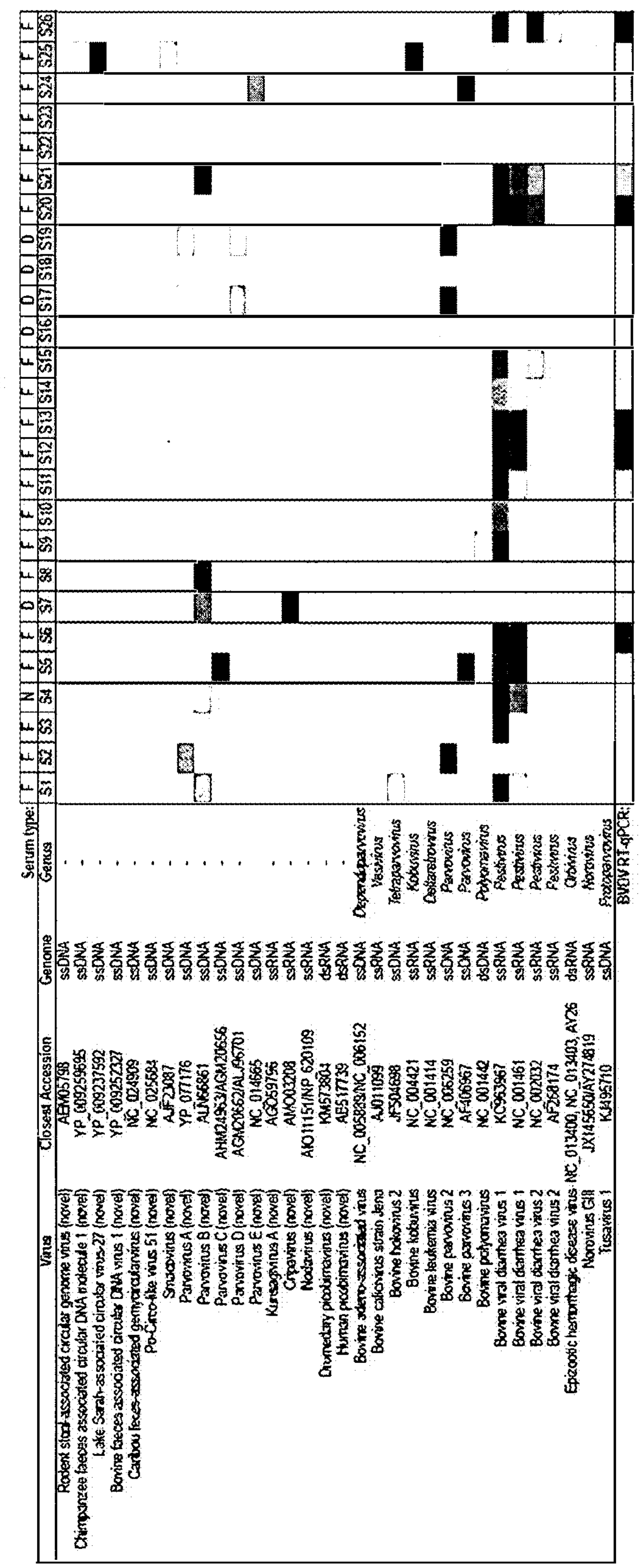
FIG. 9 shows a heat map of a number of reads with respect to several known pathogen genomes according to an example embodiment.
Figure 9:
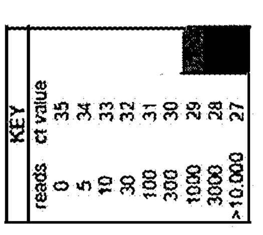

FIG. 9 illustrates a heat map 400 of a number of reads with respect to several known pathogen genomes according to experimental data utilizing an example embodiment. The experiment included 24 bovine sera and one serum each for horse, goat and sheep and a water control to establish common blood-borne livestock viruses present in commercial livestock sera. The heat map 400 illustrates experimental evidence of a plurality of viruses in the livestock sera. As such, the heat map 400 demonstrates that the methods described herein can be carried out to detect a diversity of known and novel viruses with high efficiency. Note that the heat map 400 includes detected pathogens that have single stranded DNA genomes, double stranded DNA genomes, single stranded RNA genomes, and double stranded RNA genomes.

The particular arrangements shown in the Figures should not be viewed as limiting. It should be understood that other embodiments can include more or less of each element shown in a given Figure. Further, some of the illustrated elements can be combined or omitted. Yet further, an illustrative embodiment can include elements that are not illustrated in the Figures.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method for isolating nucleic acids from a plurality of microorganisms or viruses from an environmental sample, comprising:

a. obtaining an environmental sample comprising nucleic acids from a plurality of microorganisms or viruses, b. subjecting the sample to a serial centrifugation procedure comprising, i. performing a first centrifugation under conditions that subject the nucleic acid in the sample to a force of between around 8,000×g to around 12,000×g, ii. isolating a first supernatant and a first pellet, iii. performing a second centrifugation of the first supernatant under conditions that subject the nucleic acid in the sample to a force of between about 18,000×g to about 35,000×g, in the presence or absence of a liquid centrifugation medium, and iv. retaining about 85 μl of a second supernatant comprising the plurality of microorganisms or viruses of interest, wherein the nucleic acids are isolated from the plurality of microorganisms or viruses.

2. The method of claim 1, wherein the sample is collected from a host organism comprising the plurality of microorganisms or viruses.

3. The method of claim 2, wherein the host organism is present in the environmental sample.

4. The method of claim 1, wherein the environmental sample is air, soil, or water.

5. The method of claim 1, wherein the density centrifugation medium has a density of between 1.1 and 1.5 grams per cubic centimeter.

6. The method of claim 5, wherein the density centrifugation medium is sucrose or a non-ionic, low-osmolarity liquid or iodixanol.

7. The method of claim 2, wherein nucleic acid in the sample from the host organism is removed by exposing the second supernatant, the first supernatant, or the first pellet, to one or more nucleases.

8. The method of claim 7, wherein the one or more nucleases comprises at least one of a DNA or an RNA nuclease.

9. The method of claim 1, further comprising purifying nucleic acids from the second supernatant, the first supernatant, or the first pellet.

10. The method of claim 9, further comprising purifying nucleic acids from the second supernatant, the first supernatant or first pellet, wherein the nucleic acid is DNA or RNA.

11. A method for isolating nucleic acids from a plurality of microorganisms or viruses from an aquatic or marine species, comprising:

a. obtaining the aquatic or marine species sample comprising nucleic acids from a plurality of microorganisms or viruses, b. subjecting the sample to a serial centrifugation procedure comprising, i. performing a first centrifugation under conditions that subject the nucleic acids in the sample to a force of between around 8,000×g to around 12,000×g, ii. isolating a first supernatant and a first pellet, iii. performing a second centrifugation of the first supernatant under conditions that subject the nucleic acid in the sample to a force of between about 18,000 ×g to about 35,000×g, in the presence or absence of a liquid centrifugation medium, and iv. retaining about 85 μl of a second supernatant comprising the plurality of microorganisms or viruses of interest, wherein the nucleic acids are isolated from the plurality of microorganisms or viruses.

12. A method for isolating nucleic acids from a plurality of microorganisms or viruses from a population of foodstuffs or livestock, comprising:

a. obtaining the sample of foodstuff or livestock sample comprising nucleic acid from a plurality of microorganisms or viruses, b. subjecting the sample to a serial centrifugation procedure comprising, i. performing a first centrifugation under conditions that subject the nucleic acid in the sample to a force of between around 8,000×g to around 12,000×g, ii. isolating a first supernatant and a first pellet, iii. performing a second centrifugation of the first supernatant under conditions that subject the nucleic acid in the sample to a force of between about 18,000×g to about 35,000×g, in the presence or absence of a liquid centrifugation medium, and iv. retaining about 85 μl of a second supernatant comprising the plurality of microorganisms or viruses of interest, wherein the nucleic acids are isolated from the plurality of microorganisms or viruses.

13. The method of either one of claim 11 or 12, wherein the sample is collected from a host organism comprising said plurality of microorganisms or viruses.

14. The method of claim 11, wherein aquatic species a freshwater aquatic species.

15. The method of claim 11, wherein marine species is a saltwater aquatic species.

16. A method for isolating nucleic acids from a plurality of microorganisms or viruses from a population of horses, goats, sheep pigs, or cows, comprising:

a. obtaining the horse, goats, sheep, pig, or cow sample comprising nucleic acids from a plurality of microorganisms or viruses, b. subjecting the sample to a serial centrifugation procedure comprising, i. performing a first centrifugation under conditions that subject the nucleic acid in the sample to a force of between around 8,000×g to around 12,000×g, ii. isolating a first supernatant and a first pellet, iii. performing a second centrifugation of the first supernatant under conditions that subject the nucleic acid in the sample to a force of between about 18,000×g to about 35,000×g, in the presence or absence of a liquid centrifugation medium, and iv. retaining about 85 μl of a second supernatant comprising the plurality of microorganisms or viruses of interest, wherein the nucleic acids are isolated from the plurality of microorganisms or viruses.

17. The method of any one of claim 11, 5, or 16, wherein the density centrifugation medium has a density of between 1.1 and 1.5 grams per cubic centimeter.

18. The method of claim 17, wherein the density centrifugation medium is sucrose or a non-ionic, low-osmolarity liquid or iodixanol.

19. The method of any one of claim 11, 5, or 16, wherein nucleic acid in the sample from the host organism is removed by exposing the second supernatant, the first supernatant or the first pellet, to one or more nucleases.

20. The method of claim 19, wherein the one or more nucleases comprises at least one of a DNA or an RNA nuclease.

21. The method of any one of claim 11, 5, or 16, further comprising purifying nucleic acids from any of the second supernatant, the first supernatant or first pellet, wherein the nucleic acid is DNA or RNA.

* * * * *